(12) United States Patent
Takada

(10) Patent No.: US 8,491,534 B2
(45) Date of Patent: Jul. 23, 2013

(54) PREPARATION FOR BODY SURFACE APPLICATION AND PREPARATION FOR BODY SURFACE APPLICATION-HOLDING SHEET

(75) Inventor: Kanji Takada, Kyoto (JP)

(73) Assignee: Bioserentach Co., Ltd., Kyoto (JP)

( * ) Notice: Subject to any disclaimer, the term of this patent is extended or adjusted under 35 U.S.C. 154(b) by 217 days.

(21) Appl. No.: 12/734,755

(22) PCT Filed: Nov. 21, 2008

(86) PCT No.: PCT/JP2008/071224
§ 371 (c)(1),
(2), (4) Date: Jun. 15, 2010

(87) PCT Pub. No.: WO2009/066763
PCT Pub. Date: May 28, 2009

(65) Prior Publication Data
US 2011/0028905 A1 Feb. 3, 2011

(30) Foreign Application Priority Data

Nov. 21, 2007 (JP) ................. 2007-302185
Feb. 21, 2008 (JP) ................. 2008-039814
Jul. 14, 2008 (JP) ................. 2008-182525

(51) Int. Cl.
*A61M 5/00* (2006.01)
*A61M 37/00* (2006.01)
*A61M 5/32* (2006.01)
*B28B 11/08* (2006.01)
*A61K 9/00* (2006.01)

(52) U.S. Cl.
USPC ............. 604/173; 604/46; 604/171; 604/272; 264/293; 424/400

(58) Field of Classification Search
USPC .................. 604/171, 180, 265, 892.1, 46, 48, 604/173, 289, 290, 294, 304, 307, 309, 272, 604/506; 264/255, 293; 427/2.31; 424/400
See application file for complete search history.

(56) References Cited

U.S. PATENT DOCUMENTS
2002/0082543 A1* 6/2002 Park et al. ................ 604/21

FOREIGN PATENT DOCUMENTS
JP 2003-238347 8/2003
(Continued)

OTHER PUBLICATIONS
International Search Report issued Jan. 13, 2009 in International (PCT) Application No. PCT/JP2008/071224.

*Primary Examiner* — Nicholas Lucchesi
*Assistant Examiner* — Brooke Matney
(74) *Attorney, Agent, or Firm* — Wenderoth, Lind & Ponack, L.L.P.

(57) ABSTRACT

It is an objective to provide a microneedle and a microneedle array formed from a self-dissolving base which can realize higher absorption efficiency and a higher pharmacological availability. A preparation 1 for body surface application has two sections divided in the insertion direction, namely, an acral portion 5 and a rear end portion 6. The acral portion 5 is a section including a body surface insertion end 2, and holds a target substance soluble in base. The rear end portion 6 is a section including a pressing end 3, and is formed mainly only from the base. The rear end portion 6 does not hold the target substance. When the preparation 1 for body surface application is inserted into a body surface such as the skin, since the target substance is contained in the acral portion 5, even if part of the rear end side thereof is subsequently not fully inserted into the body surface, high absorption efficiency and high pharmacological effect can be realized where the actual dose of the target substance is not below the desired amount of the drug.

20 Claims, 9 Drawing Sheets

FOREIGN PATENT DOCUMENTS

| | | |
|---|---|---|
| JP | 2005-152180 | 6/2005 |
| JP | 2005-154321 | 6/2005 |
| WO | 2006/080508 | 8/2006 |
| WO | 2007/030477 | 3/2007 |

* cited by examiner (a)

(b)

PREPARATION FOR BODY SURFACE APPLICATION AND PREPARATION FOR BODY SURFACE APPLICATION-HOLDING SHEET

This application is a U.S. national stage of International Application No. PCT/JP2008/071224 filed Nov. 21, 2008.

TECHNICAL FIELD

The present invention relates to a preparation for body surface application and a preparation for body surface application-holding sheet. The preparation for body surface application and the preparation for body surface application-holding sheet according to the present invention can efficiently administer a target substance, and can obtain high absorption rate and high pharmacological effect.

BACKGROUND ART

Microneedles (micropiles, micromissile capsules) are under study as a pharmaceutical technology to transdermally administer drugs with high efficiency, where drugs have very low bioavailability and/or low pharmacological availability by a conventional transdermal administration such as painting onto the skin. Microneedles are fine needles that do not give pain even when inserted into the skin. As the materials for microneedles, in addition to the metals used as the conventional injection needles, microneedles made of materials such as silicon have been developed (Non-Patent Documents 1 and 2). These microneedles have the same hollow structure as injection needles, and are used for the injection of drug solution.

Furthermore, self-dissolving type microneedles having biosoluble substance as a base are also developed. Where the target substance is held in the base and is administered into the epiderm followed by the self-dissolution of the base when it is inserted into the skin. For example, Patent Documents from 1 to 3 disclose self-dissolving type microneedles made of maltose as a base. Furthermore, Non-Patent Document 1 discloses self-dissolving type microneedles in which a base is made of polycaprolactone, polylactic acid, or polyglycolic acid. Patent Document 4 discloses a device or an instrument for injecting a drug via microneedles.

Patent Document 5 discloses microneedles in which a base is made of water-soluble and biosoluble thread-forming polymer. The microneedles increase skin permeability of peptides/proteins such as insulin, erythropoietin and interferon, polysaccharides such as heparin, and vitamin C that are poorly-absorbable through the skin.

Patent Document 6 discloses microneedles in which insoluble particles are localized at an acral side of a microneedle. However, because the acral side becomes brittle with this configuration, it is difficult to maintain physical strength, and there is a possibility to make problems when microneedles are inserted into the skin.

Examples in which microneedles are applied on the body surfaces other than the skin are known. For example, in Non-Patent Document 3, an example in which microneedles are applied onto the cornea is disclosed.

[Patent Document 1] Japanese Patent Laid-Open Publication No. 2003-238347
[Patent Document 2] Japanese Patent Laid-Open Publication No. 2005-154321
[Patent Document 3] Japanese Patent Laid-Open Publication No. 2005-152180
[Patent Document 4] WO 2004/000389 Pamphlet
[Patent Document 5] WO 2006/080508 Pamphlet
[Patent Document 6] WO 2007/030477 Pamphlet
[Non-Patent Document 1] D. K. Armini and C. Lui, "Microfabrication technology for polycaprolactone, a biodegradable polymer", Journal of Micromechanics and Microengineering, 2000, Vol. 10, pp. 80 to 84
[Non-Patent Document 2] M. R. Prausnitz, Microneedles for transdermal drug delivery, Advanced Drug Delivery Reviews, 2004, Vol. 56, pp. 581 to 587
[Non-Patent Document 3] J. Jiang, Coated Microneedles for Drug Delivery to the Eye, Investigative Opthalmology & Visual Science, 2007, Vol. 48, pp. 4038 to 4043

DISCLOSURE OF INVENTION

Problems to be Solved by the Invention

Based on the technology described in Patent Document 5, protein drugs like erythropoietin can be transdermally administered with high bioavailability. However, protein drugs such as erythropoietin and interferon are very expensive. Therefore, there is a need for a technology that has higher administration efficiency and make possible the higher bioavailability and pharmacological availability. The situation is the same in the case of the administration of a drug via body surfaces other than the skin.

It is an objective of the present invention to provide self-dissolving microneedles that can realize higher absorption efficiency and higher pharmacological effect.

Means for Solving the Problems

In the process of performing further research on microneedles, the present inventor has discovered a new problem. Specifically, in the conventional self dissolving type microneedle, a target substance is uniformly held in the whole base. Further, from the point of ease of handling (for example, ease of insertion into the skin), it is preferred to use microneedles having a total length of about 500 micrometers (for example, see James C. Birchall, "Chapter 18: Stratum corneum bypassed or removed" in Enhancement in Drug Delivery, ed. By Elka Touitou and Brian W. Barry, pp. 337-351, 2007, CRC Press.). However, the present inventor has discovered the phenomenon that when a microneedle with this size is inserted into the skin by pressing with a finger, total length of microneedles may not be inserted into the skin, and part of the rear end portion remains out of the skin. Consequently, in practice the target substance which is present in the rear end portion is discarded without being absorbed into the skin. The present inventor has found that this loss is an obstacle to improving bioavailability and pharmacological availability. In particular, in case that the target substance is an expensive protein drug, even if the loss is small, this is a large problem when commercializing the product. Accordingly, the present inventor continued research to solve this problem, and completed the below-described invention.

One aspect of the present invention is a needle-shaped preparation for body surface application, comprising a base formed from a biosoluble substance and a target substance held in the base, the preparation for body surface application being used by being inserted into a body surface, and the target substance being absorbed into the body by dissolution of the base, wherein the preparation for body surface application is formed of two or more sections divided in the insertion direction; the target substance is held in at least one section other than the rearmost end section; and the section in which the target substance is held is obtained by solidifying the base in which the target substance is dissolved.

The preparation for body surface application according to this aspect has a needle shape, is used by being inserted into a body surface such as the skin, the target substance is absorbed into the body by dissolution of the base. The section in which the target substance is held is composed of the "stuff obtained by solidifying the base in which the target substance is dissolved" (hereinafter, the target substance is sometimes referred to as the "target substance soluble in base"). Furthermore, the preparation for body surface application according to the present invention is formed of two or more sections divided in the insertion direction. The target substance is held in at least one section other than the rearmost end section. Therefore, when the preparation for body surface application according to this aspect is inserted into the skin and the like, even if the rearmost end section remains out of the body surface, loss of the target substance can be kept to the minimum. Consequently, higher absorption efficiency and higher pharmacological effect of the target substance can be realized.

Here, the "body surface" means a surface portion of the body which is in contact with the outside. In the present invention, the body surface includes skin, cornea, oral soft tissue, gum, nasal cavity mucosa membrane and the like. Furthermore, the "preparation for body surface application" means a preparation which can be inserted into, closely adhered to, or pasted on a body surface to administer a target substance into the body. A representative example of the preparation for body surface application is a transdermally absorbable preparation. Obviously, preparations which are used by inserting into, closely adhering to, or pasting on the cornea or the oral cavity mucosa are also included in the preparation for body surface application according to the present invention.

Another aspect of the present invention is a needle-shaped preparation for body surface application, comprising a base formed from a biosoluble substance and a target substance held in the base, the preparation for body surface application being used by being inserted into a body surface, and the target substance being absorbed into the body by dissolution of the base, wherein the preparation for body surface application is formed of two or more sections divided in the insertion direction; the target substance is held in at least one section other than the rearmost end section; and the section in which the target substance is held is obtained by solidifying (a) the base in which cells are dispersed, (b) the base in which the target substance is dispersed as a lipid dispersion, or (c) the base in which the target substance formed from fine particles having an average particle size of 10 micrometers or less is dispersed.

For the preparation for body surface application according to this aspect too, when inserted into a body surface, even if the rearmost end section remains out of the body surface, loss of the target substance can be kept to the minimum. Consequently, higher absorption efficiency and higher pharmacological effect of the target substance can be realized. Furthermore, for the preparation for body surface application according to this aspect, the section in which the target substance is held is formed from the "stuff obtained by solidifying the base in which the target substance is dispersed" (hereinafter, the target substance is sometimes referred to as the "target substance dispersible in base"), and the target substance is any of the above-described (a) to (c). Therefore, physical strength of the preparation is maintained, and insertion into the body surface is easy.

Preferably, the target substance is held in the frontmost end section.

According to this preferable aspect, the section containing the target substance is reliably inserted into the skin and the like.

Preferably, the total length in the insertion direction is in a range of 200 to 600 micrometers.

Preferably, the total length in the insertion direction is in a range of 400 to 600 micrometers.

According to this preferable aspect, especially, when inserting into the skin and the like by pressing with a finger, the section containing the target substance is reliably inserted into the skin and the like.

A sum of the lengths in the insertion direction of the sections excluding the rearmost end section is 350 micrometers or less.

According to this preferable aspect, the section containing the target substance is reliably inserted into the skin and the like.

Another aspect of the present invention is a needle-shaped preparation for body surface application, comprising a base formed from a biosoluble substance and a target substance held in the base, the preparation for body surface application being used by being inserted into a body surface, and the target substance being absorbed into the body by dissolution of the base, wherein the target substance is not uniformly distributed in the base along the insertion direction with more of the target substance present towards a tip side than a rear end side; and the portion in which the target substance is present is obtained by solidifying the base in which the target substance is dissolved.

The preparation for body surface application according to this aspect also has a needle shape, is used by being inserted into a body surface such as the skin, and the target substance is absorbed into the body by dissolution of the base. The section in which the target substance is held is formed from the "stuff obtained by solidifying the base in which the target substance is dissolved". In other words, the target substance is soluble in base. Furthermore, in the preparation for body surface application according to the present invention, the target substance is not uniformly distributed in the base along the insertion direction with more of the target substance present towards a tip side than a rear end side. Therefore, when the preparation for body surface application according to this aspect is inserted into the skin and the like, even if the rear end portion of the preparation remains out of the body surface, loss of the target substance can be kept to the minimum. Consequently, higher absorption efficiency and higher pharmacological effect of the target substance can be realized.

Another aspect of the present invention is a needle-shaped preparation for body surface application, comprising a base formed from a biosoluble substance and a target substance held in the base, the preparation for body surface application being used by being inserted into a body surface, and the target substance being absorbed into the body by dissolution of the base, wherein the target substance is not uniformly distributed in the base along the insertion direction with more of the target substance present towards a tip side than a rear end side; and the portion in which the target substance is present is obtained by solidifying (a) the base in which cells are dispersed, (b) the base in which the target substance is dispersed as a lipid dispersion, or (c) the base in which the target substance formed from fine particles having an average particle size of 10 micrometers or less is dispersed.

For the preparation for body surface application according to this aspect too, when inserted into a body surface, even if the rearmost end section remains out of the body surface, loss of the target substance can be kept to the minimum. Consequently, higher absorption efficiency and higher pharmacological effect of the target substance can be realized. Furthermore, for the preparation for body surface application according to this aspect, the target substance soluble in base is any of the above-described (a) to (c). Therefore, physical strength of the preparation is maintained, and insertion into the body surface is easy.

Preferably, the total length in the insertion direction is in a range of 200 to 600 micrometers.

Preferably, the total length in the insertion direction is in a range of 400 to 600 micrometers.

Preferably, the target substance is held in a portion within 350 micrometers from the tip towards the rear end.

Another aspect of the present invention is a needle-shaped preparation for body surface application, comprising a base formed from a biosoluble substance and a target substance held in the base, the preparation for body surface application being used by being inserted into a body surface, and the target substance being absorbed into the body by dissolution of the base, wherein the preparation for body surface application is formed of three or more sections divided in the insertion direction; the target substance is held in at least one section which is not either the frontmost end section or the rearmost end section; and the section in which the target substance is held is obtained by solidifying the base in which the target substance is dispersed.

The preparation for body surface application according to this aspect is formed of three or more sections divided in the insertion direction. The target substance (dispersible in base) is held in at least one section which is not either the frontmost end section or the rearmost end section. Therefore, when the preparation for body surface application according to this aspect is inserted into the skin and the like, even if the preparation rear end portion remains out of the body surface, loss of the target substance can be kept to the minimum. Consequently, higher absorption efficiency and higher pharmacological effect of the target substance can be realized. In addition, since the target substance is held in a section positioned nearer (rear end side) than the frontmost section, when applying to the skin for example, more of the target substance can be delivered to a closer portion in the epidermis of the skin. Still further, since the target substance (dispersible in base) is not held in the frontmost section, physical strength of the frontmost section is maintained, and insertion into the body surface is easy.

Preferably, the target substance is held in a section adjacent to the frontmost end section.

According to this preferable aspect, when applying to the skin for example, more of the target substance can be delivered to a closer portion in the epidermis of the skin.

Preferably, the total length in the insertion direction is in a range of 200 to 600 micrometers.

Preferably, the total length of the preparation in the insertion direction is in a range of 400 to 600 micrometers.

Preferably, a sum of the lengths in the insertion direction of the sections excluding the rearmost end section is 350 micrometers or less.

Preferably, the target substance comprises (i) one encapsulated in a microcapsule or (ii) fine particles having an average particle size of 10 micrometers or less.

Preferably, the body surface comprises skin, cornea, oral soft tissue, gum, or nasal cavity mucous membrane.

Preferably, the base is a high molecular weight substance.

Preferably, the high molecular weight substance is at least one kind selected from the group consisting of polysaccharides, proteins, polyvinyl alcohols, carboxy vinyl polymers, copolymers of these substances, and salts of these substances.

Preferably, the target substance is peptides, proteins, nucleic acids, or polysaccharides.

Preferably, the target substance is drugs, vaccines, nutrients, or components for cosmetics.

Preferably, the base includes a porous substance, and the target substance is held in the porous substance, so that the target substance is sustainedly released.

Yet another aspect of the present invention is a preparation for body surface application-holding sheet, in which one or two or more of the preparation for body surface application according to the present invention are held on at least one surface of a sheet-like support, wherein the preparation for body surface application can be inserted into a body surface by pressing against the body surface.

The preparation for body surface application-holding sheet according to this aspect comprises the preparation for body surface application according to the present invention. According to this aspect, the preparation for body surface application of the present invention can be easily and efficiently administered.

Preferably, the preparation for body surface application includes an adhesive substance in the rearmost end section.

According to this preferable aspect, the preparation for body surface application is reliably held by the support.

ADVANTAGES OF THE INVENTION

According to the preparation for body surface application of the present invention, a target substance can be administered via a body surface with higher absorption efficiency and higher pharmacological effect. Consequently, the preparation for body surface application of the present invention is especially useful when the target substance is expensive.

Similarly, for the preparation for body surface application-holding sheet according to the present invention, a target substance can be administered via a body surface with higher absorption efficiency and higher pharmacological effect. Furthermore, the preparation for body surface application according to the present invention can be easily and efficiently administered.

BRIEF DESCRIPTION OF THE DRAWINGS

FIG. 8(b) is a perspective view illustrating a preparation for body surface application according to yet another embodiment of the present invention.

Figure 1:
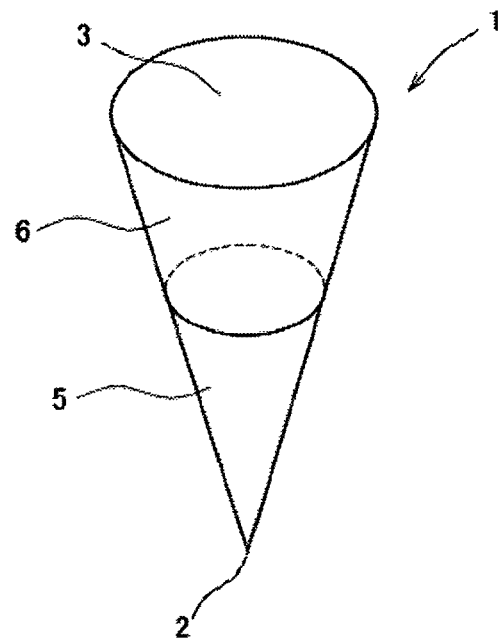
FIG. 1 is a perspective view illustrating a preparation for body surface application according to a first embodiment of the present invention.

DESCRIPTION OF THE REFERENCE NUMERALS 1, 1a to 1i . . . Preparation for body surface application,
2 . . . Body surface insertion end (tip),
3 . . . Pressing end (rear end),
5 . . . Tip portion (section),
6, 6a to 6i . . . Rear end portion (section),
7, 7a to 7c . . . Middle portion (section),
8 . . . Skin (body surface),
21, 22, 23, 25, 26 . . . Preparation for body surface application,
50 . . . Preparation for body surface application-holding sheet,
58 . . . Support.

BEST EMBODIMENT FOR CARRYING OUT THE INVENTION

Figure 2:
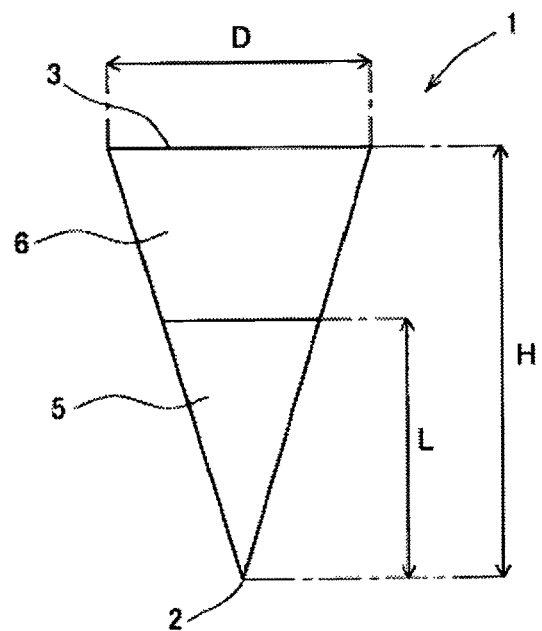
FIG. 2 is a front view of the preparation for body surface application of FIG. 1.

A best embodiment for carrying out the invention will now be described. As illustrated in FIGS. 1 and 2, a preparation 1 for body surface application according to a first embodiment of the present invention is a solid preparation which is generally called microneedles, micropiles, micromissile capsules and the like. This preparation 1 for body surface application has a needle shape, specifically, a cone shape. The preparation 1 for body surface application has a body surface insertion end 2 with a tapered shape at the frontmost end thereof, and a pressing end 3 at the rearmost end formed in a roughly circular flat surface. The preparation 1 for body surface application is used by being inserted into the body surface such as the skin by pressing the pressing end 3 in a state in which the body surface insertion end 2 is in contact with the body surface.

The preparation 1 for body surface application has a total length H of approximately 500 micrometers ($\mu m$). The pressing end 3 has a diameter D of approximately 300 $\mu m$. The possible ranges for the total length H of the preparation 1 for body surface application and the diameter D of the pressing end 3 thereof are not especially limited, as long as the values allow the preparation 1 for body surface application to be used as microneedles. For example, H has a value which may be selected from the range of 50 to 1,500 $\mu m$, preferably 100 to 1,000 $\mu m$, more preferably 200 to 600 $\mu m$, and still more preferably 400 to 600 $\mu m$. In particular, when the preparation is inserted into the body surface by pressing with a finger, a range of 400 to 600 $\mu m$ is easy to use. Furthermore, D has a value which may be selected from the range of, for example, 50 to 500 $\mu m$, preferably 100 to 450 $\mu m$, and more preferably 200 to 400 $\mu m$. From the perspective of strength, D is preferably $\frac{1}{2}$ of H to the same value as H, and more preferably $\frac{2}{3}$ of H to the same value as H.

In the preparation 1 for body surface application, the target substance is not uniformly distributed (localized) in the base along the insertion direction, and the content density of the target substance at the side of the body surface insertion end 2 is larger than the content density of the target substance at the side of the pressing end 3. Specifically, the preparation 1 for body surface application has two sections divided in the insertion direction, namely, a tip portion 5 and a rear end portion 6. The tip portion 5 is a section including the body surface insertion end 2, and is formed from the base which holds the target substance. More specifically, the tip portion 5 is formed from the "stuff obtained by solidifying the base in which the target substance is dissolved". In other words, the target substance is soluble in base. Consequently, the target substance is present in the base as a solid dispersion or a supramolecular complex. On the other hand, the rear end portion 6 is a section including the pressing end 3, and is formed mainly only from the base. The rear end portion 6 does not hold the target substance. The boundary between the tip portion 5 and the rear end portion 6 is a roughly flat surface. Specifically, while in the conventional self-dissolving type microneedles the target substance is uniformly held in the base, in the preparation 1 for body surface application of the present embodiment, the target substance is held non-uniformly with a bias in the base. The base is made from biosoluble substances.

The tip portion 5 has a length L in the insertion direction of approximately 300 $\mu m$. The possible range for L may be appropriately selected based on the insertable depth into the body surface. For example, when the preparation is inserted into the body surface by pressing with a finger, L is preferably 350 $\mu m$ or less, and more preferably 300 $\mu m$ or less. While the lower limit is not especially limited, it may be, for example, 100 $\mu m$ or more. Concerning the pressure when inserting the microneedle into the skin by hand (manual insertion into the skin), there is a disclosure of 0.35 to 0.5 N (Kolli et al., Pharmaceutical Research, Vol. 25, pp. 104 to 113 (2007)).

Figure 3:
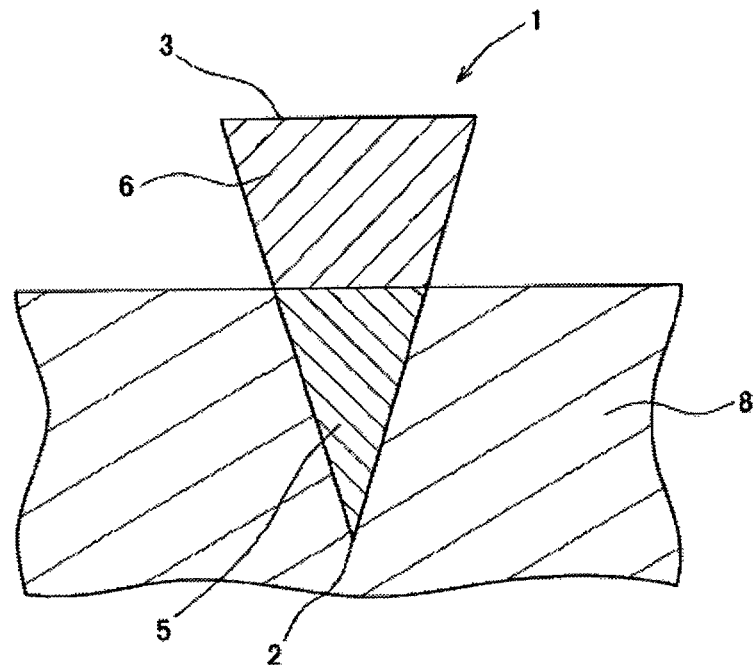
FIG. 3 is a cross-sectional view illustrating a state in which the preparation for body surface application of FIG. 1 is inserted into the skin.

FIG. 3 illustrates a state in which the preparation 1 for body surface application is inserted into skin (body surface) 8 by pressing with a finger. When the preparation 1 for body surface application is inserted into the skin 8 by pressing with a finger, usually only about 300 to 350 $\mu m$ of the tip side is inserted into the skin 8. About 150 to 200 $\mu m$ of the rear end side remains outside the skin 8. However, in the preparation 1 for body surface application, the target substance is contained in the tip portion 5. Therefore, as shown in FIG. 3, even if part or all of the rear end portion 6 is not inserted into the skin 8 and remains outside of the skin 8, high absorption efficiency and high pharmacological effect can be realized where the actual dose of the target substance does not decrease below its desired dose. Furthermore, since the target substance is not contained in the rear end portion 6, the target substance is not wasted, so that economical effect is high. Therefore, from a practical standpoint, the effects are very high.

In the present embodiment, the target substance held in the tip portion 5 is soluble in base. However, the target substance may also be used in the tip portion 5 even if it is dispersible in base. Specifically, the stuff obtained by solidifying (a) the base in which cells are dispersed, (b) the base in which a target substance is dispersed as lipid dispersion, or (c) the base in which a target substance formed from fine particles having an average particle size of 10 micrometers or less is dispersed, may be used. If the target substance is dispersible in base like (a) to (c), problems do not especially occur during insertion into the body surface since physical strength of the tip portion 5 is maintained.

Examples of the cell of (a) include red blood cells. Further, examples of the lipid dispersion of (b) include liposome preparations, emulsions and the like. In addition, while the fine particles of (c) preferably have an average particle size of 10 micrometers or less, more preferred is 5 µm or less, and even more preferred is 2 µm or less. More specifically, if the average particle size is more than 10 µm, the section becomes brittle, which makes it difficult to maintain physical strength of the tip portion 5. Consequently, the tip portion 5 is crushed during insertion into the skin and the like, so that insertion becomes difficult.

In the present embodiment, although the rear end portion 6 is formed only from biosoluble base, an adhesive substance may optionally be formulated.

Although the method for producing the preparation 1 for body surface application is not especially limited, a method which uses a mold may be used, for example. First, a mold having cone-shaped pores is prepared. Then, a substance for forming the base is dissolved with a solvent, and a target substance is further dissolved or dispersed therein to prepare a liquid base that contains the target substance. This liquid base containing target substance is charged into the cone-shaped mold, whereby a tip portion 5 is formed. At this stage, it is preferred to perform centrifugation or to apply pressure so that the liquid base reaches right into the depths of the mold. Next, a liquid base which does not contain the target substance is prepared and further charged into the mold so as to be superimposed over the target substance-containing base. Consequently, a rear end portion 6 is formed. Then, the bases are solidified, and a cone-shaped solid stuff is removed from the mold. The produced solid stuff is formed as the needle-shaped preparation 1 for body surface application having two sections (tip portion 5 and rear end portion 6) as illustrated in FIGS. 1 and 2.

Figure 4:
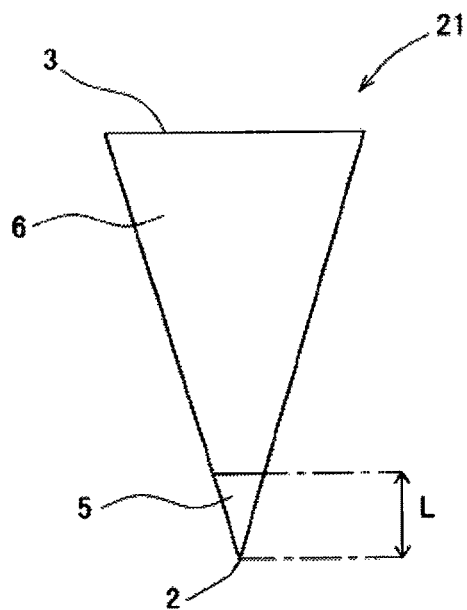
FIG. 4 is a front view illustrating a modified example of the preparation for body surface application of FIG. 1.

In the preparation 1 for body surface application, the length L in the insertion direction of the tip portion 5 is approximately 300 µm. However, this length L may be even shorter. Although a preparation for body surface application 21 shown in FIG. 4 has the same external form as the preparation 1 for body surface application shown in FIGS. 1 and 2, the length L of the acral portion 5 is approximately 100 µm. The target substance is concentrated in the portion near the body surface insertion end 2.

The preparations for body surface application 1 and 21 are both divided into two or more sections. However, the present invention is not limited to these embodiments. Specifically, as long as the target substance is not uniformly distributed (localized) in the base along the insertion direction, and the content density of the target substance at the side of the body surface insertion end 2 is larger than the content density of the target substance at the side of the pressing end 3, the portion containing the target substance and the other portions do not have to be divided with a clear interface. For example, the content density of the target substance may gradually increase from the pressing end 3 towards the body surface insertion end 2, so that the density change is continuous.

Figure 5:
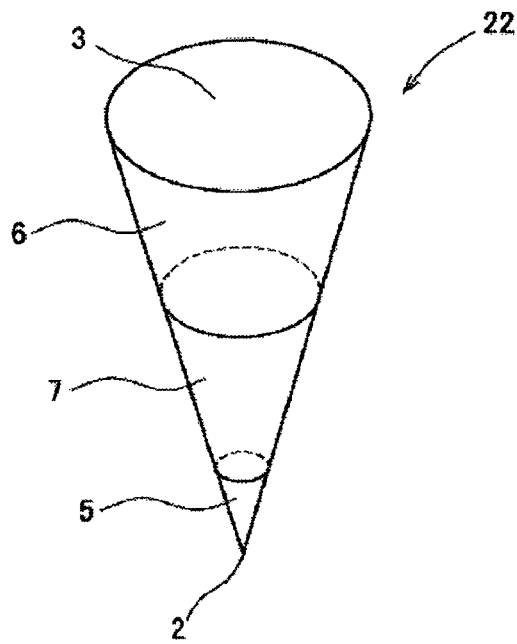
FIG. 5 is a perspective view illustrating a preparation for body surface application according to a second embodiment of the present invention.
Figure 6:
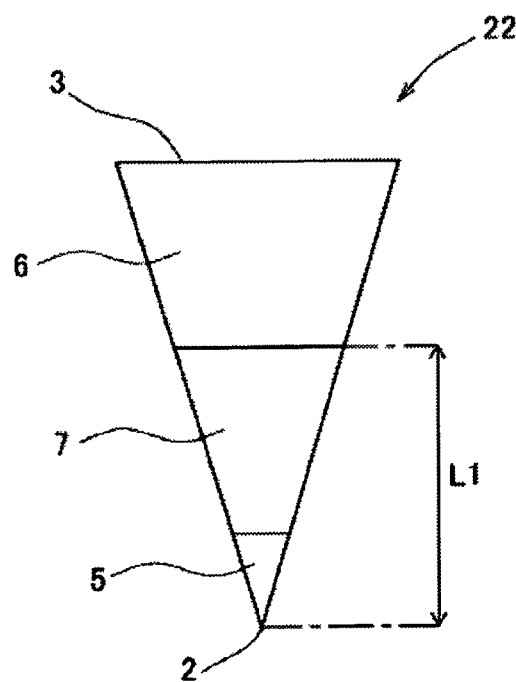
FIG. 6 is a front view of the preparation for body surface application of FIG. 5.

A preparation 22 for body surface application according to a second embodiment illustrated in FIGS. 5 and 6 has three sections divided in the insertion direction. More specifically, a middle portion 7 is arranged between the tip portion 5 including the body surface insertion end 2 and the rear end portion 6 including the pressing end 3. The target substance is held in the middle portion 7. The middle portion 7 is formed from the "stuff obtained by solidifying the base in which the target substance is dispersed". In other words, the target substance held in the middle portion 7 is dispersible in base. On the other hand, the tip portion 5 and the rear end portion 6 are both sections formed mainly only from a base. These portions do not hold the target substance. The length of the portions in the preparation 22 for body surface application excluding the rear end portion 6, namely, a sum length L1 of the tip portion 5 and the middle portion 7, is approximately 300 µm, which is about the same as the length of the acral portion 5 of the preparation 1 for body surface application illustrated in FIGS. 1 and 2. Therefore, if the preparation 22 for body surface application is inserted into the body surface such as the skin by pressing with a finger, usually all of the middle portion 7 will enter the body surface. Consequently, high absorption efficiency and high pharmacological effect of the target substance can be realized. In addition, when applying to the skin for example, more of the target substance can be delivered to the epidermis than to the dermis. Still further, since the target substance dispersible in base is not held in the tip portion 5, physical strength of the tip portion 5 is high. Consequently, insertion of the preparation 22 for body surface application into the body surface is easy. The preparation 22 for body surface application can be obtained by, for example, superimposing in order the liquid bases corresponding to the tip portion 5, the middle portion 7, and the rear end portion 6 on the above-described cone-shaped mold, and solidifying the liquid bases.

Representative examples of the target substance dispersible in base held in the middle portion 7 include a target substance formed from the microparticles insoluble in base. Examples of such a target substance include (i) a target substance encapsulated in a microcapsule; and (ii) a target substance of microparticles having an average particle size of 10 µm or less.

When using a target substance soluble in base or a target substance dispersible in base as described in the (a) to (c), the target substance may be held in the tip portion 5, or may be held in both the middle portion 7 and the tip portion 5. Furthermore, different target substances may be held in the middle portion 7 and the tip portion 5, respectively. For example, a target substance dispersible in base may be held in the middle portion 7 and a target substance soluble in base may be held in the tip portion 5.

Figure 7:
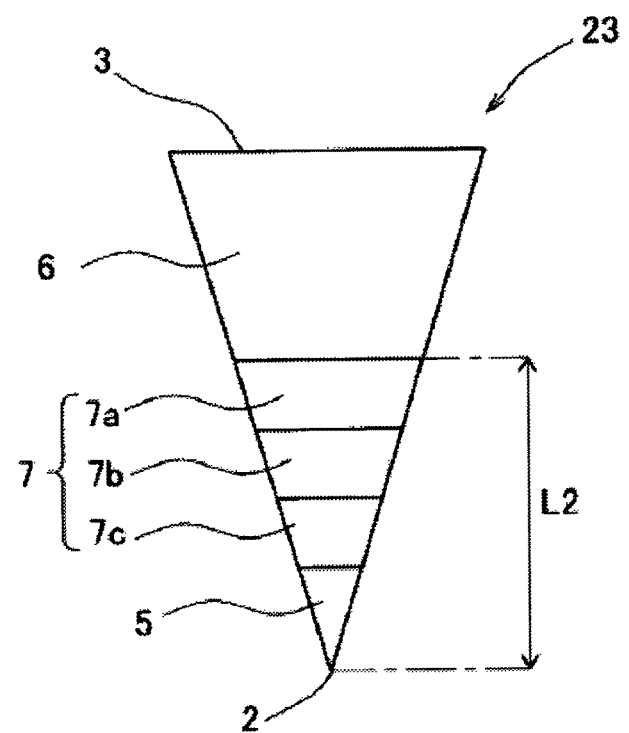
FIG. 7 is a front view illustrating a modified example of the preparation for body surface application of FIG. 5.

The middle portion may be formed of a plurality of sections. The preparation 23 for body surface application illustrated in FIG. 7 has five sections divided in the insertion direction, namely, a tip portion 5, middle portions 7a, 7b, and 7c, and a rear end portion 6. Specifically, the preparation 22 for body surface application has three middle portions 7a, 7b, and 7c between the tip portion 5 and the rear end portion 6. The middle portions 7a, 7b, and 7c are layered in that order. The middle portion 7a is in contact with the rear end portion 6, and the middle portion 7c is in contact with the tip portion 5. The length of the portions in the preparation 23 for body surface application excluding the rear end portion 6, namely, a sum length L2 of the acral portion 5 and the middle portions 7a, 7b, and 7c, is approximately 300 micrometers, which is about the same as the length of the acral portion 5 of the preparation 1 for body surface application illustrated in FIGS. 1 and 2. According to the preparation 23 for body surface application, for example, different target substances dispersible in base may be held in the middle portions 7a, 7b, and 7c, respectively. Obviously, a target substance soluble in base or a target substance dispersible in base as described in the (a) to (c) may also be held in the tip portion 5.

In the above-described embodiments, although the rear end portion 6 does not contain the target substance, the present invention is not limited to this. For example, the present invention also includes an aspect in which a small amount of a target substance is unintentionally contained in the rear end portion 6.

Figure 8:
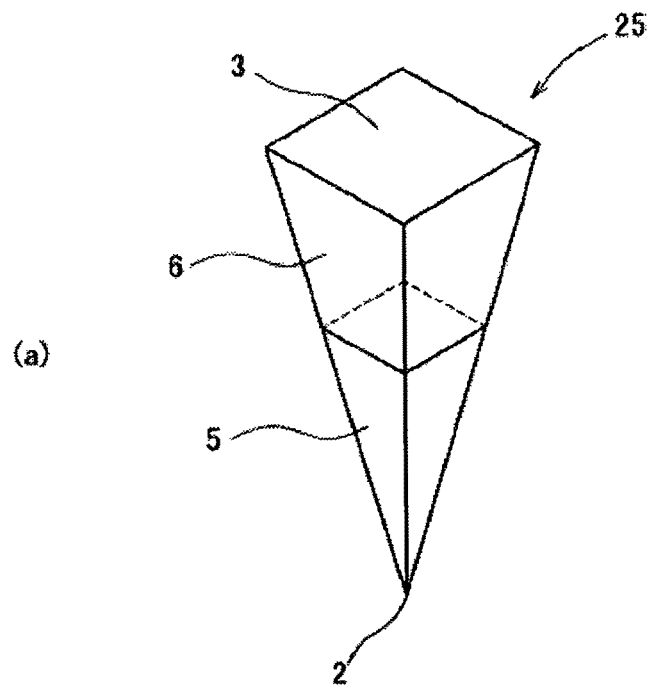
FIG. 8($a$) is a perspective view illustrating a preparation for body surface application according to another embodiment of the present invention.
Figure 8:
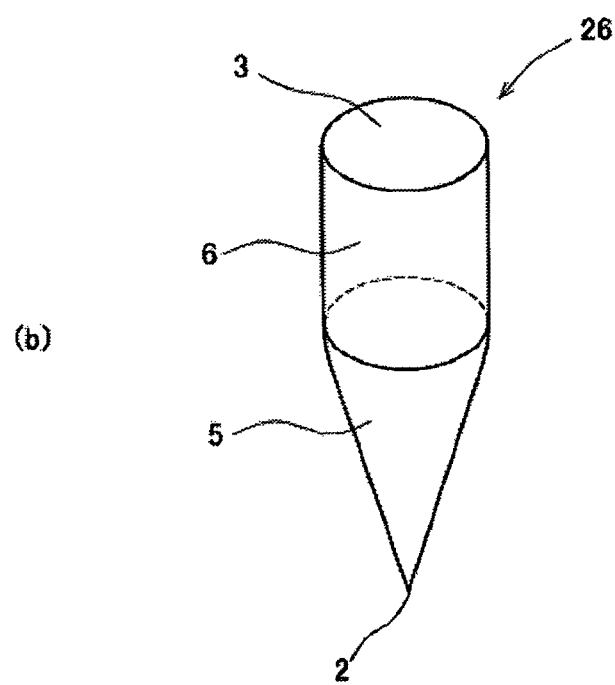

In the above-described embodiments, while all of the preparations for body surface application had a cone-shaped external form, the present invention is not limited to this shape. As long as the preparation for body surface application is "needle-shaped", another shape may be employed. Specifically, any shape generally considered to be a microneedle, micropile, micromissile capsule shape or the like is included in the present invention. For example, the four-sided pyramid-shaped preparation 25 for body surface application illustrated in FIG. 8(a), and the nail-shaped preparation 26 for body surface application illustrated in FIG. 8(b) are included in the needle-shaped preparation for body surface application according to the present invention. In addition, all of the shapes of the transdermal absorption preparation described in WO 2006/080508 pamphlet are also included in the "needle shaped". Furthermore, a neck or a cleavage line may also be provided on the surface of the preparation for body surface application according to the present invention.

Figure 9:
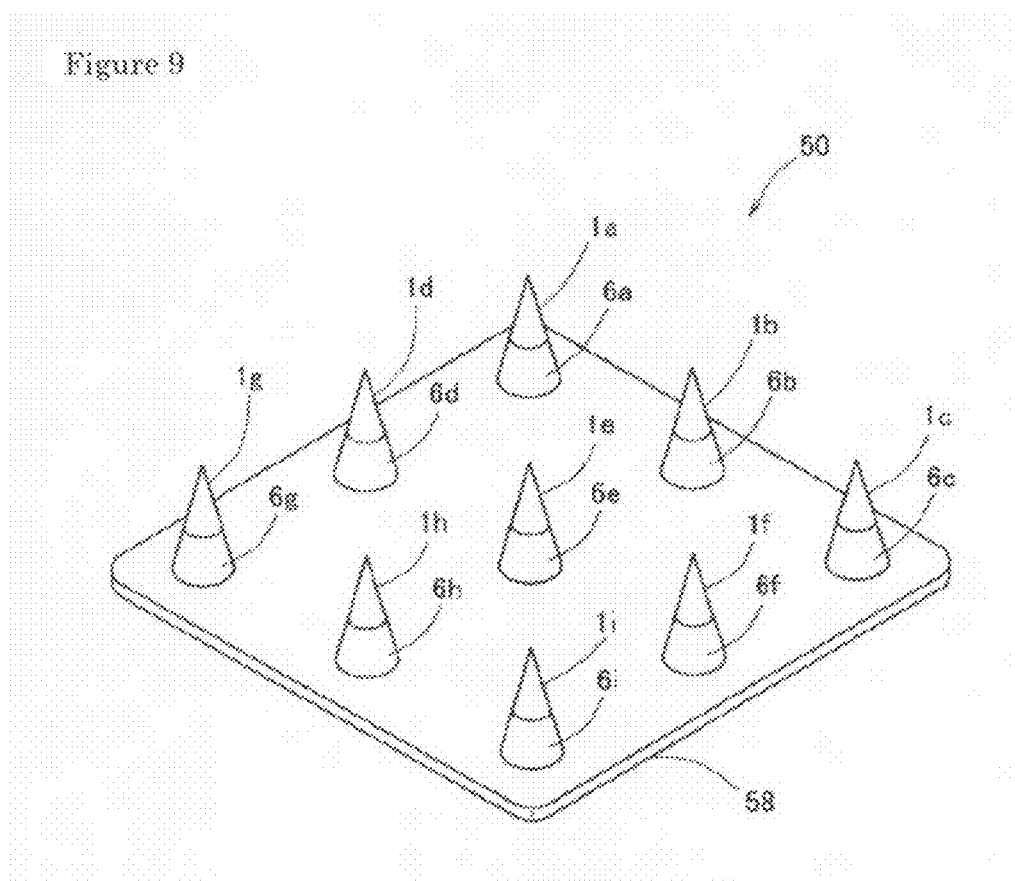
FIG. 9 is a perspective view illustrating a preparation for body surface application-holding sheet according to an embodiment of the present invention.

Next, an embodiment of a preparation for body surface application-holding sheet according to the present invention will be described. A preparation for body surface application-holding sheet 50 shown in FIG. 9 is a patch made of a sheet-like support 58 and nine preparations 1a to 1i for body surface application. The preparations 1a to 1i for body surface application are held on one surface of the support 58. Furthermore, the preparations 1a to 1i for body surface application can be inserted by pressing the preparation for body surface application-holding sheet 50 into a body surface such as the skin. The preparation for body surface application-holding sheet 50 is also called as the "microneedle array". The preparations 1a to 1i for body surface application have the same basic structure as the preparation 1 for body surface application illustrated in FIGS. 1 and 2. However, the preparations 1a to 1i for body surface application contain an adhesive substance in respective rear end portions 6a to 6i. Consequently, the preparations 1a to 1i for body surface application can be reliably held on the support 58 via the rear end portions 6a to 6i. Examples of adhesive substances which can be used include substances and materials employed for the adhesive tape of pharmaceuticals, such as acrylic acids, acrylates, copolymers thereof, and silicone-based adhesives and the like. It is preferred that the support 58 is formed from a material which has a stable strength. However, the support 58 may also be formed from a flexible material. For example, a paper board or various kinds of medical tape such as a cloth adhesive bandage can be employed as the support 58. Further, after pressing the preparation for body surface application-holding sheet 50 against the body surface, the support 68 may be pasted on the body surface as it is, or only the support 58 may be peeled off and removed. In the former case, an adhesive substance may be coated on the whole pasting surface of the support 58 so that the support 58 is reliably pasted on the body surface.

Next, the base and the target substance will be described. The base used in the preparation for body surface application according to the present invention is formed from a biosoluble substance. This substance may be a high molecular weight substance or a low molecular weight substance (for example, maltose).

In a preferred embodiment, the base is formed from a high molecular weight substance. In a more preferred embodiment, the high molecular weight substance is at least one kind selected from the group consisting of polysaccharides, proteins, polyvinyl alcohols, carboxy vinyl polymers, copolymers of these substances, and salts of these substances. One kind of such high molecular weight substances may be used, or the combination of a plurality of kinds may be used. Further, polysaccharides, proteins, polyvinyl alcohols, and carboxy vinyl polymers are all the high molecular weight substances which are water soluble and thread-formable.

Examples of polysaccharides include hyaluronic acid, chondroitin sulfate, dextran, dextran sulfate, alginic acid, glycogen, hydroxypropyl cellulose, hydroxypropyl methylcellulose phthalate, agarose, chitin, chitosan, pectin, and pullulan, and salts thereof. One kind of such a polysaccharide may be used, or the combination of a plurality of kinds may be used. Examples of the protein include serum albumin, serum a acidic glycoprotein, gelatin, and salts thereof. One kind of such a protein may be used, or a combination of a plurality of kinds may be used. Obviously, the polysaccharide and the protein may be used in combination.

On the other hand, the target substance is not especially limited. Any substance may be used as the target substance, for example a high molecular weight substance, a low molecular weight substance, a chemical substance, a physiologically active substance, proteins (recombinant or natural), peptides, polysaccharides and the like. Preferred examples include peptides, proteins, nucleic acids, or polysaccharides. As described above, cells may also be used as the target substance. Furthermore, as the application, a configuration in which the target substance comprises drugs, vaccines, nutrients, or components for cosmetics is also preferred. If the target substance is a drug or a vaccine (a vaccine antigen), the preparation for body surface application of the present invention can be used in the treatment, prevention, diagnosis and the like of a disease. Furthermore, if the target substance is a component for cosmetics, the preparation for body surface application of the present invention can be used for purposes of prevention and improvement of skin aging, anti-aging, skin whitening maintenance, and the like. Examples of the nutrients include health foods and functional food components. Although specific examples of substances which can be employed as the target substance in the preparation for body surface application according to the present invention will now be described below, the target substance of the present invention is not limited to these.

[Examples of Transdermally Poorly- or Low-Absorbable High Molecular Weight Substances]

Examples include: insulin; interferon; erythropoietin (EPO); tumor necrosis factor (TNF); granulocyte colony-stimulating factor (G-CSF); granulocyte-monocyte colony-stimulating factor (GM-CSF); calcitonin; chorionic gonadotropin; desmopressin acetate; growth hormone; vaccines such as influenza vaccine, hepatitis vaccine, and polio vaccine; leuprorelin acetate; Botulinum toxin; glucocerebrosidase; factor VII; ovary-stimulating hormone; ghrelin; various growth factors such as platelet-derived growth factor (PDGF); and nucleic acids such as DNA, RNA, oligo nucleotides (for example, for antisense).

[Examples of Transdermally Poorly- or Low-absorbable Drugs]

Examples include diclofenac and the like.

[Examples of Drugs for Corneal Administration]

Examples include pilocarpine hydrochloride and the like.

[Examples of Drugs for Oral Cavity Mucosal Membrane Administration]

Examples include lidocaine hydrochloride and the like.

[Examples of Nutrients]

Examples include vitamin C (ascorbic acid) and the like.

[Examples of a Component for a Cosmetic]

Examples include retinol and the like.

The preparation for body surface application according to the present invention can be used as a sustained-release preparation. In one embodiment, the base includes a porous substance. The target substance is held in the porous substance, and is sustainedly released. Examples of the porous substance include silicates such as calcium silicate, aluminum silicate, and magnesium silicate; anhydrous silicic acid; porous carbonates such as porous calcium carbonate; porous phosphates such as porous calcium phosphate; porous silicon and the like. One kind of such a porous substance may be used, or a combination of a plurality of kinds may be used.

In another embodiment, the target substance is a long-acting type substance, and the target substance is sustainedly released. Examples of long-acting type substances include long-acting insulin, and polyethylene glycol (PEG)-crosslinked proteins. Specific examples of long-acting insulin include intermediate-, long-, and super long-acting insulins. Specific examples of PEG-crosslinked proteins include PEG-modified proteins such as PEG-interferon and PEG-erythropoetin.

According to the present invention, a method for administering a target substance is provided, in which a needle-shaped preparation for body surface application is inserted into a body surface so that the target substance is absorbed into the body. Similarly, a method for administering a target substance is provided in which a preparation for body surface application-holding sheet is attached on a body surface so that the target substance is absorbed into the body.

The present invention will now be described in more detail based on the following examples. However, the present invention is not limited to these examples.

EXAMPLE 1

One hundred (10 lines×10 columns) inverted cone-shaped pores having a depth of approximately 500 micrometers (μm) and a basement diameter of approximately 300 micrometers were arranged on a surface of a substrate made of a silicon resin which was a square with a bottom face 1 cm long and 1 cm wide. This substrate was used as the mold for production of microneedle (preparation for body surface application) or patch/microneedle array (preparation for body surface application-holding sheet). This mold was used in the present example as well as in the subsequent examples.

A viscous dense solution (solution A1) was prepared by adding 80 microliters (μL) of purified water to 30 mg of insulin sodium salt (self-prepared product; target substance), 0.2 mg of evans blue (Nacalai Tesque, Inc.), and 30 mg of chondroitin sulfate C sodium salt (Wako Pure Chemical Industries, Ltd.; base), and thoroughly dissolving and mixing the resultant mixture. Furthermore, a dense solution (solution B1) was prepared by adding 30 μL of purified water to 30 mg of chondroitin sulfate C sodium salt and 0.5 mg of Hiviswako 103 (Wako Pure Chemical Industries, Ltd.; adhesive substance), and thoroughly dissolving and mixing the resultant mixture. In addition, an adhesive (solution C1) was prepared by adding 36 mL of purified water to 1.6 g of Hiviswako 103, and thoroughly dissolving and mixing the resultant mixture.

Solution A1 was coated and filled into each of the mold pores, and the surface was then covered with a wrapping film (Saran Wrap®; Asahi Kasei Corporation). The mold was set in a table-top centrifuge (Kubota 4000), and centrifuged for 5 minutes at 3,000 rpm. Consequently, the solution A1 was filled into the pores more towards the deeper end (tip side) of the pores, so that a space was formed at the near side (rear end side) of the pores.

The wrapping film was taken off, and residue on the mold surface was removed. Next, the solution B1 was coated and filled into each of the mold pores, and the surface was then covered with a wrapping film. The mold was set in a table-top centrifuge, and centrifuged for 5 minutes at 3,000 rpm. Consequently, the solution B1 was filled into the pores, and superimposed over the solution A1. The solution C1 was coated on a paper sheet (support), then covered and pasted onto the whole surface of the mold. The mold was centrifuged for 5 minutes at 3,000 rpm by a table-top centrifuge to dry and solidify each of the viscous solutions in the mold. The paper sheet was slowly peeled off, so that the needle-shaped solid stuff (microneedles) was removed from the mold while still held on the paper sheet. Consequently, a patch/microneedle array (preparation for body surface application-holding sheet) holding 100 microneedles (preparations for body surface application) was obtained. Any of the 100 microneedles held on the sheet had two sections as illustrated in FIGS. 1 and 2, namely, an acral portion containing the insulin sodium salt and a rear end portion containing the adhesive substance. The tip portions were colored blue due to the presence of the evans blue.

EXAMPLE 2

A dense solution was prepared by adding 80 μL of purified water to 30 mg of chondroitin sulfate C sodium salt (Wako Pure Chemical Industries, Ltd.; base). A viscous, dense suspension (solution A2) was prepared by adding to this dense solution 30 mg of diclofenac sodium salt (Wako Pure Chemical Industries, Ltd.; target substance) produced to have a particle size of about 5.0 μm by pulverizing it with a mortar made from agate, and mixing the resultant mixture. Furthermore, an adhesive solution (solution B2) was prepared by adding 35 mL of purified water to 1.6 g of Hiviswako 103, and dissolving the resultant mixture. In addition, a dense solution (solution C2) was prepared by adding 0.8 mL of purified water to 300 mg of chondroitin sulfate C sodium salt, and thoroughly dissolving the resultant mixture.

In the same manner as in Example 1, the solution A2 was coated and filled into each of the mold pores, and then centrifuged (3,000 rpm, 5 minutes). Consequently, the solution A2 was filled into the pores more towards the deeper end (tip side) of the pores, so that a space was formed at the near side (rear end side) of the pores. The wrapping film was removed, and residue on the mold surface was removed. Next, the solution B2 was thinly coated over the whole of the mold surface. In addition, the solution C2 was placed over each of the mold pores, and a paper sheet (support) was covered and pasted thereon. The mold was centrifuged by a table-top centrifuge (3,000 rpm, 30 minutes). Consequently, the solution C2 was filled into the pores, and superimposed over a solution A3. Simultaneously, the respective solutions in the mold were dried and solidified. The paper sheet was slowly peeled off, so that the needle-shaped solid stuff was removed from the mold while still held on the paper sheet. Consequently, a patch/microneedle array holding 100 microneedles was obtained. Any of the 100 microneedles held on the sheet had two sections as illustrated in FIGS. 1 and 2, namely, an acral portion containing the diclofenac sodium salt and a rear end portion formed from only the base. The acral portions were colored white due to the presence of the diclofenac sodium salt. The length L of the acral portions was approximately 350 μm.

EXAMPLE 3

An insulin solution having a concentration of 9.6 mg/mL was prepared by dissolving insulin sodium salt (self-prepared product; target substance) in purified water. A 0.1 mL insulin solution was added to 15.9 mg of porous anhydrous silicic acid (trade name: Sylysia 350; Fuji Sylysia Chemical Ltd.; porous substance) (average particle size: 3.9 μm), and the resultant mixture was thoroughly mixed and then dried. Consequently, an insulin-adsorbed powder was obtained in which insulin was held on the porous anhydrous silicic acid. A paste-like base solution was prepared by adding 800 μL of purified water to 300 mg of chondroitin sulfate C sodium salt (Nacalai Tesque, Inc.; base), and thoroughly dissolving and mixing the resultant mixture. A dense solution (solution A3) was then prepared by adding the insulin-adsorbed powder to this base solution, and thoroughly mixing the resultant mixture. Furthermore, an adhesive solution (solution B3) was prepared by adding 35 mL of purified water to 1.5 mg of chondroitin sulfate C sodium salt and 50 mg of Hiviswako 103, and thoroughly dissolving and mixing the resultant mixture.

In the same manner as in Example 1, the solution A3 was coated and filled into each of the mold pores, and then centrifuged (3,000 rpm, 3 minutes). Consequently, the solution A3 was filled into the pores more towards the deeper end (tip side) of the pores, so that a space was formed at the near side (rear end side) of the pores. The wrapping film was removed, and residue on the mold surface was removed. The solution B3 was placed over each of the mold pores, and coated over the whole of the mold surface. Then, the mold was centrifuged by a table-top centrifuge (3,000 rpm, 30 minutes). Consequently, the solution B3 was filled into the pores, and superimposed over the solution A3. Simultaneously, the respective thick liquids in the mold were dried and solidified. A sheet of filter paper (support) moistened with purified water was pasted on the mold surface, then slowly peeled off, so that the needle-shaped solid stuff was removed from the mold while still held on the filter paper. Consequently, a patch/microneedle array (preparation for body surface application-holding sheet) holding 100 microneedles (preparations for body surface application) was obtained. Any of the 100 microneedles held on the sheet had two sections as illustrated in FIGS. 1 and 2, namely, an acral portion containing the insulin sodium salt held on the porous anhydrous silicic acid and a rear end portion formed of only the base, from which the insulin sodium salt was to be sustainedly released.

EXAMPLE 4

A viscous base solution was prepared by adding 20 mL of purified water to 2.0 g of hyaluronic acid (Foodchemifa Co., Ltd., trade name: FCH-SU), and then uniformly stirring the resultant mixture with a homogenizer. A dense solution (solution A4) was prepared by dissolving 20 mg of ascorbic acid (Nacalai Tesque, Inc.; target substance) in 50 μL of purified water, then adding 2.1 g of the base solution, and thoroughly mixing the resultant mixture. Furthermore, an adhesive (solution B4) was prepared by adding 1.0 g of the base solution to 1 mg of Hiviswako 103, and thoroughly mixing the resultant mixture.

The solution A4 was degassed. In the same manner as in Example 1, the solution A4 was coated and filled into each of the mold pores, and then centrifuged (3,000 rpm, 5 minutes). Consequently, the solution A4 was filled into the pores more towards the deeper end (tip side) of the pores, so that a space was formed at the near side (rear end side) of the pores. The wrapping film was taken off, and residue on the mold surface was removed. Then, the solution B4 was placed over each of the mold pores, and coated over the whole of the mold surface. The mold was centrifuged by a table-top centrifuge (3,000 rpm, 30 minutes). Consequently, the solution B4 was filled into the pores, and superimposed over the solution A4. Simultaneously, the respective solutions in the mold were dried and solidified. A paper sheet (support) coated with the solution B4 was pasted on the mold surface, then slowly peeled off, so that the needle-shaped solid stuff was removed from the mold while still held on the paper sheet. Consequently, a patch/microneedle array holding 100 microneedles was obtained. Any of the 100 microneedles held on the sheet had two sections as illustrated in FIGS. 1 and 2, namely, an acral portion containing ascorbic acid and a rear end portion formed from only the base.

EXAMPLE 5

A viscous, dense solution (solution A5) was prepared by adding 120 of purified water to 7.5 mg of insulin sodium salt (self-prepared product; target substance), 0.2 mg of evans blue, and 52.5 mg of chondroitin sulfate C sodium salt (Wako Pure Chemical Industries, Ltd.; base), and thoroughly dissolving and mixing the resultant mixture. Furthermore, a dense solution (solution B5) was prepared by adding 30 μL of purified water to 30 mg of chondroitin sulfate C sodium salt and 0.5 mg of Hiviswako 103, and thoroughly dissolving and mixing the resultant mixture. In addition, an adhesive (solution C5) was prepared by adding 36 mL of purified water to 1.6 g of Hiviswako 103, and dissolving the resultant mixture.

Figure 10:
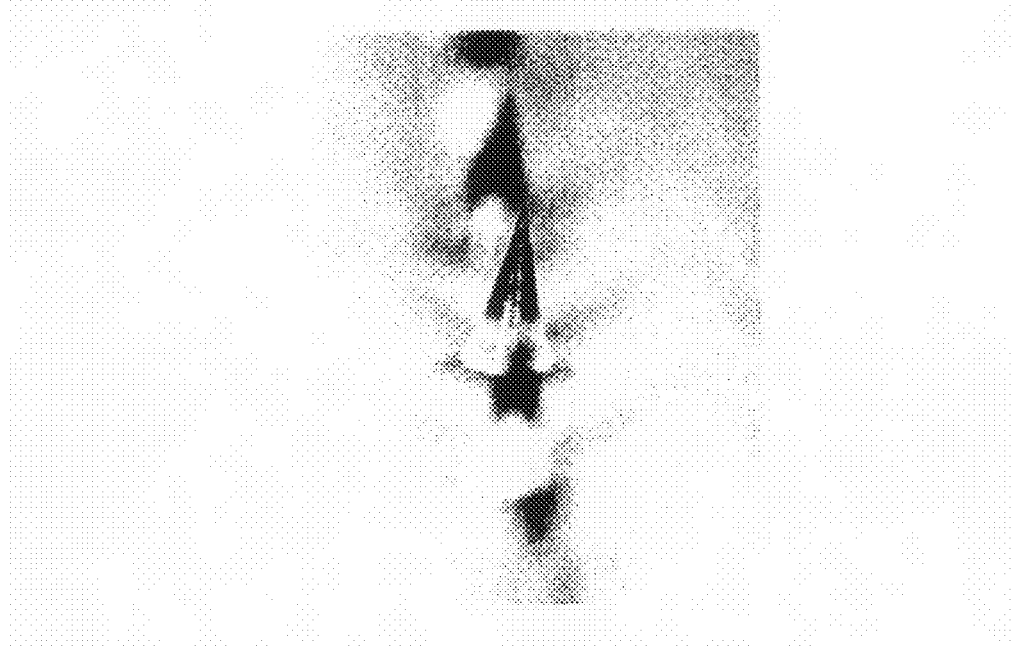
FIG. 10 is a photograph of the microneedle array produced in Example 5.

The solution A5 was put on the tip of a 27G syringe needle, and dispensed into each of the pores of the mold of Example 1 in an atmosphere humidified with water vapor. In the same manner as in Example 1, the surface was covered by a wrapping film, and then the mold was centrifuged (3,000 rpm, 2 minutes). Consequently, the solution A5 was filled into the pores more towards the deeper end (tip side) of the pores, so that a space was formed at the near side (rear end side) of the pores. Furthermore, the solution B5 was coated and filled into each of the mold pores (spaces), and centrifuged (3,000 rpm, 5 minutes). Consequently, the solution B5 was filled into the pores, and superimposed over the solution A5. The solution C5 was coated on the surface of a paper sheet (support), then pasted on the surface of the mold. The mold was centrifuged in that state (3,000 rpm, 30 minutes), so that the respective solutions in the mold were dried and solidified. A cloth adhesive bandage (Nichiban (registered trademark); Nichiban Co., Ltd.) was further pasted over the paper sheet, then slowly peeled off, so that the needle-shaped solid stuff was removed from the mold while still held on the paper sheet. Consequently, a patch/microneedle array holding 100 microneedles was obtained. Any of the 100 microneedles held on the sheet had two sections as illustrated in FIGS. 1 and 2, namely, an acral portion containing the insulin sodium salt and a rear end portion containing the adhesive substance. The acral portions were colored blue due to the presence of the evans blue. The length L of the acral portions was approximately 200 to 300 μm. FIG. 10 shows a photograph of the microneedle array produced in the present example. In the acral portion of each microneedle (colored black in the photograph) insulin and evans blues are present.

Evaluation of the microneedles in the present example was carried out simultaneously with the following Example 6.

EXAMPLE 6

A viscous, dense solution (solution A6) was prepared by adding 120 μL of purified water to 3.75 mg of insulin sodium salt (self-prepared product; target substance), 0.2 mg of evans blue, and 56.25 mg of chondroitin sulfate C sodium salt (Wako Pure Chemical Industries, Ltd.; base), and thoroughly dissolving and mixing the resultant mixture. A patch/microneedle array holding 100 microneedles was obtained in the same manner as in Example 5, except that the solution A6 was used instead of the solution A5. The length of the acral portions (blue) of the microneedles was approximately 200 to 300 μm. The respective microneedles produced in Examples 5 and 6 were subjected to the following evaluations.

[Measurement of Insulin Content]

One hundred microneedles were collected from each patch produced in Examples 5 and 6, and placed in a 1.5 mL capacity sample cup for centrifugal separation. The microneedles were dissolved with 1.0 mL phosphate buffer. One hundred μL of the resultant mixture was subjected to HPLC to measure the insulin content.

Then the content per patch (mean value) for each example was calculated. The results were that the patch from Example 5 was 0.70 IU and the patch from Example 6 was 0.37 IU.

[Test Using Rat]

Figure 11:
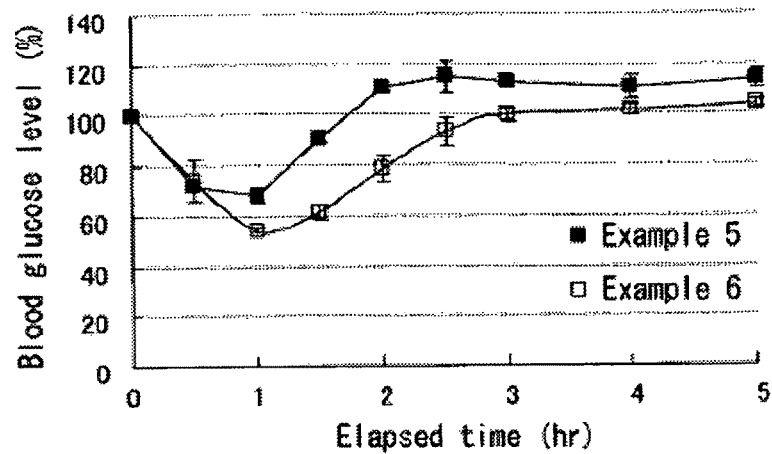
FIG. 11 is a graph showing the temporal transitions of the blood glucose level after the microneedles produced in Examples 5 and 6 were administered to a rat.

Male Wistar rats having the body weight of approximately 350 g was secured to an operating table under the anesthesia with pentobarbital, and the hair from the abdomen was removed. At this stage, first, approximately 0.2 mL of blood was collected from the jugular vein. Next, one patch from Example 5 or 6 was pressed against the abdominal skin of the rat from which hair had been removed to administer insulin to the skin. Blood was collected from the jugular vein for 5 hours after administration, and systemic blood was collected. A serum sample was obtained from each of the obtained blood specimens, and the serum glucose level (blood sugar level) was measured using a glucose assay kit (Glucose C-II Test Wako; Wako Pure Chemical Industries, Ltd.). The respective blood glucose levels are expressed as the relative value with respect to the pre-dose blood glucose level of 100%. All of the data was calculated as the mean±SD of 3 or 4 rats per group. The results are shown in FIG. 11. In FIG. 11, the data indicated with black square are the results for the preparation of Example 5, and the data indicated with white square are the test results for the preparation of Example 6. As is clear from FIG. 11, all of the preparations showed the minimum blood glucose level at 1 hour after administration, and thus the effect of insulin was observed.

Using different group of rats, the insulin solution was administered by subcutaneous injection at 1.0 IU/kg to study the temporal transitions of the hypoglycemic effect. By comparing with the hypoglycemic effect, the pharmacological availability of insulin from each patch/microneedle array was calculated. As a result, the preparation of Example 5 showed 35.7±7.0%, and the preparation of Example 6 showed 36.3±2.6%. It was thus shown that insulin can be administered from the skin with high absorption efficiency by the patch of either Example 5 or 6.

EXAMPLE 7

A viscous, dense solution (solution A7) was prepared by kneading 46 μL of an erythropoietin injection liquid (trade name: Espo Subcutaneous Injection; 24,000 units/0.5 mL; Kirin Brewery Company Limited; target substance), with 0.5 mg of evans blue, and 45 mg of chondroitin sulfate C sodium salt (base). Furthermore, dense solution (solution B7) was prepared by adding 620 μL of purified water to 600 mg of chondroitin sulfate C sodium salt and 5 mg of Hiviswako 103, and thoroughly dissolving and mixing the resultant mixture. In addition, adhesive solution (solution C7) was prepared by adding 36 mL of purified water to 1.6 g of Hiviswako 103, and thoroughly dissolving and mixing the resultant mixture.

In the same manner as in Example 1, the solution A7 was coated and filled into each of the mold pores, and then centrifuged (4,000 rpm, 5 minutes). Consequently, the solution A7 was filled into the pores more towards the deeper end (tip side) of the pores, so that a space was formed at the near side (rear end side) of the pores. Furthermore, the solution B7 was coated and filled into each of the mold pores (spaces), and centrifuged (3,000 rpm, 15 minutes). Consequently, the solution B7 was filled into the pores, and superimposed over the solution A7. Simultaneously, the respective dense solutions in the mold were dried and solidified. The solution C7 was coated on the surface of a paper sheet (support), then pasted on the surface of the mold, and centrifuged in that state (3,000 rpm, 30 minutes) to dry. The paper sheet was slowly peeled off, so that the needle-shaped solid stuff was removed from the mold while still held on the paper sheet. Consequently, a patch/microneedle array holding 100 microneedles was obtained. Any of the 100 microneedles held on the sheet had two sections as illustrated in FIGS. 1 and 2, namely, an acral portion containing erythropoietin (EPO) and a rear end portion containing the adhesive substance.

Evaluation of the microneedles in the present example was carried out simultaneously with the following Example 8.

EXAMPLE 8

Erythropoietin injection solution was concentrated by a factor of two under a nitrogen gas flow. A viscous, dense solution (solution A8) was prepared by kneading 46 μL of this dense solution, with 0.5 mg of evans blue, and 45 mg of chondroitin sulfate C sodium salt (base). A patch/microneedle array holding 100 microneedles was obtained in the same manner as in Example 7, except that the solution A8 was used instead of the solution A7. Any of the 100 microneedles held on the sheet had two sections as illustrated in FIGS. 1 and 2, namely, an acral portion contained EPO and a rear end portion contained the adhesive substance. The respective microneedles produced in Examples 7 and 8 were subjected to the following evaluations.

[Measurement of EPO Content]

One hundred microneedles were collected by the same procedure as in Example 6, and the EPO content (mean value) per patch produced in Examples 7 and 8 was calculated. The EPO content was measured using an EPO Elisa Kit (Roche Diagnostics KK). As the results, the patch from Example 7 had an EPO content of 12.5±1.5 IU and the patch from Example 8 had an EPO content of 31.3±5.9 IU.

[Rat Experiments]

Figure 12:
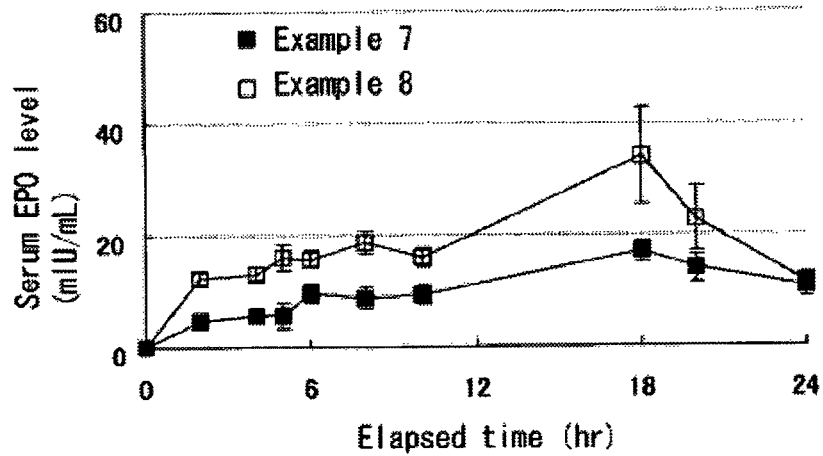
FIG. 12 is a graph showing the temporal transitions of serum EPO level after the microneedles produced in Examples 7 and 8 were administered to a rat.

The experiment was carried out basically by the same procedures as in Example 6. Three or four rats were used per group. Blood was collected from the jugular vein for 24 hours after EPO administration, and the systemic blood was collected. Using the EPO Elisa Kit, the serum EPO concentrations were measured. The results are shown in FIG. 12. In FIG. 12, the data indicated by black square are the results for the preparation of Example 7 (low dose group), and the data indicated by white square are the results for the preparation of Example 8 (high dose group). As is clear from FIG. 12, all of the preparations showed an increase in the serum EPO level in proportion with the EPO content in the microneedles. Thus, a good dose-dependency was obtained.

Using different group of rats, the EPO injection solution was administered by subcutaneous injection at the dose of 1.0 IU/kg. The mean value of the area under the serum EPO level-time curve (AUC) after administration was determined, and the bioavailability was calculated. As the result, the preparation of Example 7 (low dose group) had 30% as the mean value, and the preparation of Example 8 (high dose group) had the mean value of 29%. It was thus shown that EPO can be administered from the skin with high absorption efficiency by the microneedles of either Example 7 or 8.

EXAMPLE 9

Egg albumin (OVA) was employed as a model antigen. A solution was made by adding 9.0 mL of purified water to 4.0 mg of egg albumin (egg albumin (crude); Nacalai Tesque, Inc.; target substance) and 5.0 mg of evans blue to dissolve. A viscous, dense solution (solution A9) was prepared by adding 8.5 g of chondroitin sulfate C sodium salt to the above solution. Further, dense solution (solution B9) was prepared by adding 1.0 mL of purified water to 1.0 mg of chondroitin sulfate C sodium salt and 0.5 mg of Hiviswako 103, and thoroughly dissolving and mixing the resultant mixture.

The solution A9 was put on the tip of a 27G syringe needle, and dispensed into each of the pores of the mold of Example 1 in an atmosphere humidified with water vapor. The mold was placed in an acrylic resin case, and then centrifuged (3,000 rpm, 3 minutes) in the same manner as in Example 1. Consequently, the solution A9 was filled into the pores more towards the deeper end (tip side) of the pores, so that a space was formed at the near side (rear end side) of the pores. The mold was taken out of the case, and residue on the mold surface was removed. Furthermore, the solution B9 was coated on each of the mold pores (spaces). A paper sheet (support) was placed over the mold, and both ends of the sheet were fixed by a cloth adhesive bandage. Then, the mold was centrifuged (3,000 rpm, 30 minutes). Consequently, the solution B9 was filled into the pores, and superimposed over the solution A9. Simultaneously, the respective dense solution in the mold were dried and solidified. The paper sheet was slowly peeled off, so that the needle-shaped solid stuff was removed from the mold while still held on the paper sheet. Consequently, a patch/microneedle array holding 100 microneedles was obtained. Any of the 100 microneedles held on the sheet had two sections as illustrated in FIGS. 1 and 2, namely, an acral portion containing OVA and a rear end portion containing the adhesive substance. The acral portions were colored blue due to the presence of the evans blue. The length L of the acral portions was approximately 300 to 350 μm.

Five BALB/c mice having body weight of approximately 30 g were used as one group. The mice were secured to an operating table under anesthesia with pentobarbital, and the hair from their backs was removed. Next, one patch from the present example was pressed against the backs of the mice whose hair had been removed to administer OVA from the skin. Two weeks after administration, OVA was again administered using one patch. Two weeks after the second administration, all of the blood was collected. As a positive control group, OVA was administered as an aqueous solution by subcutaneous injection to a second group of different mice at the dose of 1.0 microgram (Comparative Example 1) or 0.1 microgram (Comparative Example 2) at the zero week and second week, and similarly all of the blood was collected after 2 weeks had elapsed from the second administration. Using the obtained serum specimens, the OVA antibody titer was measured. The results were that when the microneedles obtained in the present example were administered, an antibody titer between that of Comparative Example 2 (subcutaneous injection of 0.1 micrograms) and Comparative Example 1 (subcutaneous injection of 1.0 microgram) was shown.

EXAMPLE 10

A standard buffer (Nacalai Tesque, Inc.) having a pH of 4.01 was diluted by a factor of 10 with purified water (dilute buffer). Then, 5.0 mg of pilocarpine hydrochloride (Nacalai Tesque, Inc.) was dissolved in 10 mL of the above dilute buffer and 4.0 mL of ethyl alcohol. Furthermore, 500 mg of hydroxypropyl methylcellulose phthalate (HPMCP; Variety HP-55S; Shin-Etsu Chemical Co. Ltd.; base) was added, and the resultant mixture was stirred at about 40° C. to dissolve. After dissolving, the mixture was further stirred under warm air to concentrate to the viscosity at which the mixture could be easily coated on the mold (solution A10). Furthermore, dense solution (solution B10) was prepared by adding 1.0 mL of degassed purified water to 1.0 g of chondroitin sulfate C sodium salt, and thoroughly dissolving and mixing the resultant mixture.

In the same manner as in Example 1, the solution A10 was coated and filled into each of the mold pores. In the same manner as in Example 9, the mold was placed in an acrylic resin case, and then centrifuged (3,000 rpm, 30 minutes). Consequently, the solution A10 was filled into the pores more towards the deeper end (tip side) of the pores, so that a space was formed at the near side (rear end side) of the pores. Furthermore, in the same manner as in Example 9, the solution B10 was coated and filled into each of the mold pores (spaces), and centrifuged (3,500 rpm, 5 minutes). Consequently, the solution B10 was filled into the pores, and superimposed over the solution A10. The mold was moved to a desiccator, so that the respective dense solutions in the mold were dried and solidified. The needle-shaped solid stuff was removed from the mold to obtain 100 microneedles. Any of the 100 microneedles had two sections as illustrated in FIGS. 1 and 2, namely, an acral portion containing pilocarpine and a rear end portion containing chondroitin sulfate C sodium salt.

Under ether anesthesia, 20 microneedles from the present examples were inserted into the eyeball cornea of rabbits, and the state of the pupil was observed. As a result, pupil constriction effect appeared at 30 minutes after administration and the maximum miotic rate was 63%.

EXAMPLE 11

A dense solution (solution A11) was prepared by adding 10 μL of sumatriptan (trade name: Imigrane Nasal Drops; target substance; equivalent to 2.0 mg of sumatriptan) and 140 μL of purified water to 0.5 mg of methylene blue (Nacalai Tesque, Inc.) and 5.0 mg of hyaluronic acid (trade name: FCH-60; Foodchemifa Co., Ltd.; base), and thoroughly dissolving and mixing the resultant mixture. Further, dense solution (solution B11) was prepared by adding 1.0 mL of degassed purified water to 1.0 g of high molecular weight dextran (Nacalai Tesque, Inc.).

In the same manner as in Example 9, the solution A11 was dispensed into each of the mold pores, and then centrifuged (3,500 rpm, 15 minutes). Consequently, the solution A11 was filled into the pores more towards the deeper end (tip side) of the pores, so that a space was formed at the near side (rear end side) of the pores. The mold was taken out of the case, and residue on the mold surface was removed. The mold was further centrifuged (3,500 rpm, 15 minutes). Subsequently, in the same manner as in Example 9, coating of the solution B11, pasting and centrifuging of the paper sheet, and drying were carried out. After the drying, the paper sheet was slowly peeled off and the needle-shaped solid stuff on the paper sheet was removed from the mold. Consequently, a patch/microneedle array holding 100 microneedles was obtained. Any of the 100 microneedles held on the sheet had two sections as illustrated in FIGS. 1 and 2, namely, an acral portion containing sumatriptan and a rear end portion containing the high molecular weight dextran. The acral portions were colored blue due to the presence of the methylene blue. The length L of the acral portions was approximately 300 to 350 µm.

Male Wistar rats (3 or 4 rats) having the body weight of approximately 330 g were secured to an operating table under anesthesia with pentobarbital, and then the hair from their abdomen was removed. Approximately 0.2 mL of blood was collected from the jugular vein, and then one patch produced in the present example was pressed against the abdominal skin of the rats whose hair had been removed to administer sumatriptan from the skin. Blood was collected from the jugular vein for 3 hours after administration, and systemic blood was collected. Plasma samples were obtained by centrifugation, and the plasma sumatriptan concentrations were measured by an LC/MS/MS method. The results are shown in Table 1. The values in the table are the mean values of 3 to 4 experiments. Specifically, a good plasma sumatriptan levels were obtained by transdermal administration.

filled into the pores more towards the deeper end (tip side) of the pores, so that a space was formed at the near side (rear end side) of the pores. Next, the solution B12 was coated and filled into each of the mold pores (spaces), and also coated on the mold surface. A paper sheet was pasted on the mold surface, and both ends were fixed by a tape. Then, the mold was centrifuged (3,500 rpm, 30 minutes). Consequently, the solution B12 was filled into the pores, and superimposed over the solution A12. Simultaneously, the respective dense solutions in the mold were dried and solidified. The paper sheet was slowly peeled off and the needle-shaped solid stuff held on the paper sheet was removed from the mold. Consequently, a patch/microneedle array holding 100 microneedles was obtained. Any of the 100 microneedles held on the sheet had two sections as illustrated in FIGS. 1 and 2, namely, an acral portion containing human growth hormone and a rear end portion. The length L of the tip portions was approximately 250 µm.

In the same manner as in Example 1, one patch of the present example was pressed against the skin of 2 rats to administer human growth hormone. Blood was collected from the jugular vein for 4 hours after administration, and systemic blood was collected. Plasma samples were obtained by centrifugation, and the plasma human growth hormone

TABLE 1

| | Time (min) | | | | | | | | | | |
| --- | --- | --- | --- | --- | --- | --- | --- | --- | --- | --- | --- |
| | 0 | 2 | 5 | 10 | 15 | 20 | 30 | 45 | 60 | 120 | 180 |
| Sumatriptan concentration (ng/mL) | ND | 7.2 | 35.3 | 38.1 | 27.5 | 21.5 | 17.5 | 11.2 | 8.1 | 3.0 | 1.8 |

ND: Not detected

EXAMPLE 12

A viscous, dense solution (solution A12) was prepared by adding 90 µL of degassed purified water to 5.0 mg of recombinant human growth hormone (Wako Pure Chemical Industries, Ltd.; target substance), 35 mg of chondroitin sulfate C sodium salt, and 0.5 mg of lissamine green B (MP Biomedicals LLC), and thoroughly dissolving and mixing the resultant mixture. Further, dense solution (solution B12) was prepared by adding 1 mL of degassed purified water to 1.0 g of chondroitin sulfate C sodium salt, and thoroughly dissolving and mixing the resultant mixture.

In the same manner as in Example 1, the solution A12 was coated and filled into each of the mold pores. In the same manner as in Example 9, the mold was placed in an acrylic resin case, and then centrifuged (3,500 rpm, 10 minutes). The mold was taken out from the case, and centrifuged further (3,500 rpm, 5 minutes). Consequently, the solution A12 was level in each sample was measured by an hGH-Elisa Kit (Biosource). The results are shown in Table 2. The values in the table are the mean value of 2 experiments. The area under the plasma drug concentration-time curve, AUC, was obtained and compared with the AUC value obtained by intravenous study of hGH to calculate bioavailability. A value of approximately 90% was obtained.

TABLE 2

| | Time (min) | | | | | | | | |
| --- | --- | --- | --- | --- | --- | --- | --- | --- | --- |
| | 0 | 15 | 30 | 45 | 60 | 90 | 120 | 180 | 240 |
| Growth hormone concentration (ng/mL) | ND | 32.4 | 31.6 | 28.2 | 23.8 | 16.6 | 12.8 | 5.0 | 2.3 |

ND: Not detected

EXAMPLE 13

A viscous, dense solution (solution A13) was prepared by adding 50 µL of degassed purified water to 5.0 mg of tacrolimus (FK506; Sigma; target substance) which had been subjected to fine pulverization using a mortar made from agate, 0.5 mg of evans blue, and 25 mg of chondroitin sulfate C sodium salt, and thoroughly mixing the resultant mixture. Further, dense solution (solution B13) was prepared by adding 1.0 mL of degassed purified water to 1.0 g of chondroitin sulfate C sodium salt, and dissolving and kneading the resultant mixture. In addition, another dense solution (solution C13) was prepared by adding 1.5 mL of degassed purified water to 1.0 g of chondroitin sulfate C sodium salt, and dissolving and mixing the resultant mixture.

The solution C13 was put on the tip of a 27G syringe needle, coated on each of the mold pores, and dried while centrifuging (3,000 rpm, 15 minutes). Consequently, the solution C13 was filled into the pores more towards the deeper end (tip side) of the pores, so that a space was formed at the near side (rear end side) of the pores. Then, in the same manner as in Example 1, the solution A13 was coated and filled into each of the mold pores. In the same manner as in Example 9, the mold was placed in an acrylic resin case, and then centrifuged (3,500 rpm, 15 minutes). The mold was taken out from the case, and centrifuged further (3,500 rpm, 5 minutes). Consequently, the solution A13 was filled into the pores, and superimposed over the solution C13. However, a space was left on the near side (rear end side) of the pores. Next, the solution B13 was coated and filled into each of the mold pores (spaces), and also coated on the mold surface. A paper sheet was pasted on the mold surface, and both ends were fixed by a tape. Then, the mold was centrifuged (3,500 rpm, 20 to 30 minutes). Consequently, the solution B13 was filled into the pores, and superimposed over the solution A13. Simultaneously, the respective dense solutions in the mold were dried and solidified. The paper sheet was slowly peeled off and the needle-shaped solid stuff held on the paper sheet was removed from the mold. Consequently, a patch/microneedle array holding 100 microneedles was obtained. Any of the 100 microneedles held on the sheet had three sections as illustrated in FIGS. 5 and 6, namely, a tip portion formed from the base, a middle portion containing tacrolimus, and a rear end portion. The middle portions were colored blue due to the presence of the evans blue.

In the same manner as in Example 1, one patch of the present example was pressed against the skin of 2 rats to administer tacrolimus. Blood was collected from the jugular vein for 24 hours after administration, and systemic blood was collected. Plasma sample was prepared from each of the obtained blood sample. Tacrolimus was extracted from plasma sample by solid extraction method and was measured using LC/MS/MS. The results are shown in Table 3. The values in the table are the mean value of 2 examples. The results show that while tacrolimus was detected in the plasma, its concentrations were very low. Calculating the bioavailability by comparing with the area under the plasma tacrolimus level-time curve, AUC, obtained after intravenous injection of tacrolimus gave a value of approximately 0.3%. It was thought that tacrolimus was delivered to a site near the skin after administration to the skin.

TABLE 3

| | Time (hr) | | | | | | | | |
| --- | --- | --- | --- | --- | --- | --- | --- | --- | --- |
| | 0 | 1 | 2 | 3 | 4 | 5 | 6 | 9 | 12 | 24 |
| Tacrolimus concentration (ng/mL) | ND | 0.4 | 0.6 | 0.6 | 0.5 | 0.5 | 0.5 | 0.5 | 0.5 | 0.5 |

ND: Not detected

EXAMPLE 14

1.0 mg of desmopressin (DDAVP; Wako Pure Chemical Industries, Ltd.; target substance) was dissolved in 50 μL of a pH 6.5 phosphate buffer. Then, a viscous, dense solution (solution A14) was prepared by further adding 0.5 mg of evans blue and 25 mg of chondroitin sulfate C sodium salt, and mixing the resultant mixture. Further, viscous solution (solution B14) was prepared by adding 1.0 mL of degassed purified water to 1.0 g of chondroitin sulfate C sodium salt, and dissolving and mixing the resultant mixture.

In the same manner as in Example 1, the solution A14 was coated and filled into each of the mold pores. Subsequently, by the same procedures as in Example 13, centrifuging (3,500 rpm, 15 minutes), centrifuging (3,500 rpm, 20 minutes), coating of the solution B14, pasting of the paper sheet, and centrifuging (3,500 rpm, 20 to 30 minutes) were carried out. The paper sheet was slowly peeled off and the needle-shaped solid stuff held on the paper sheet was removed from the mold. Consequently, a patch/microneedle array holding 100 microneedles was obtained. Any of the 100 microneedles held on the sheet had two sections as illustrated in FIGS. 1 and 2, namely, acral portion containing desmopressin and a rear end portion. The acral portions were colored blue due to the presence of evans blue.

Figure 13:
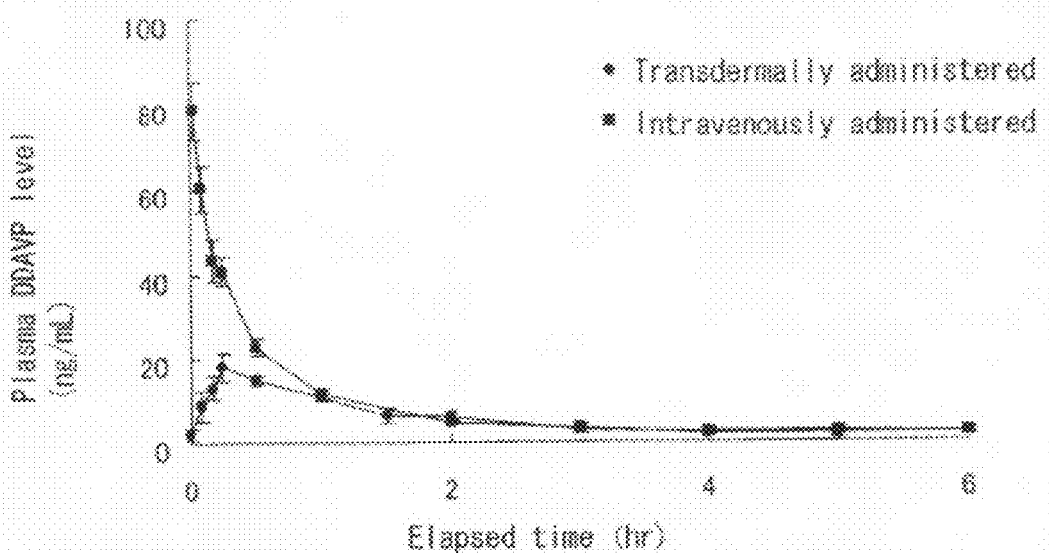
FIG. 13 is a graph showing the temporal transitions of plasma desmopressin level after the microneedles produced in Example 14 were administered to a rat, and temporal transitions after intravenous injection.

In the same manner as in Example 1, one patch of the present example was pressed against the skin of 3 to 4 rats to administer approximately 10 μg/kg of desmopressin. Blood was collected from the jugular vein for 6 hours after administration, and systemic blood was collected. Plasma sample was prepared from each of the obtained blood sample. Desmopressin in each plasma sample was extracted by solid phase extraction method, and its concentration was measured using LC/MS/MS. As a control, desmopressin was intravenously administered to different group of rats, 15 μg/kg. The results are shown in FIG. 13. In FIG. 13, the data indicated by a black circle are the experimental results for the case when the preparation of the present example was transdermally administered, and the data indicated by a black square are the experimental results for the case when desmopressin was intravenously administered. The values in the graph show the mean±SD of 3 to 4 experiments. Specifically, when the preparation of the present example was administered, the percutaneous absorption efficiency was approximately 100%.

EXAMPLE 15

A viscous, dense solution (solution A15) was prepared by adding 100 μL of degassed purified water to 10.0 mg of heparin sodium salt (Nacalai Tesque, Inc.; target substance), 0.5 mg of evans blue, and 35 mg of chondroitin sulfate C sodium salt, and dissolving and mixing the resultant mixture. Further, a viscous solution (solution B15) was prepared by adding 1.0 mL of degassed purified water to 1.0 g of chondroitin sulfate C sodium salt, and dissolving and mixing the resultant mixture.

By the same procedures as in Example 14, coating of the solution A15 into each pore, centrifuging (3,500 rpm, 10 minutes), centrifuging (3,500 rpm, 5 minutes), coating of the solution B15, pasting of the paper sheet, and centrifuging (3,500 rpm, 30 minutes) were carried out. The paper sheet was slowly peeled off and the needle-shaped solid stuff held on the paper sheet was removed from the mold. Consequently, a patch/microneedle array holding 100 microneedles was obtained. Any of the 100 microneedles held on the sheet had two sections as illustrated in FIGS. 1 and 2, namely, a tip portion containing heparin and a rear end portion. The acral portions were colored blue due to the presence of the evans blue. The length L of the acral portions was approximately 300 μm.

EXAMPLE 16

Rifampicin (Wako Pure Chemical Industries, Ltd.; target substance) was pulverized using an agate mortar. A viscous, dense solution was prepared by adding 65 µL of degassed purified water to 0.5 mg of evans blue and 25 mg of chondroitin sulfate C sodium salt, and mixing the resultant mixture. A dense suspension (solution A16) was prepared by adding 5.0 mg of the pulverized rifampicin product to the above dense solution. Further, a viscous solution (solution B16) was prepared by adding 1.0 mL of degassed purified water to 1.0 g of chondroitin sulfate C sodium salt, and dissolving and mixing the resultant mixture. In addition, another viscous solution (solution C16) was prepared by adding 1.5 mL of degassed purified water to 1.0 g of chondroitin sulfate C sodium salt, and dissolving and mixing the resultant mixture.

Figure 14:
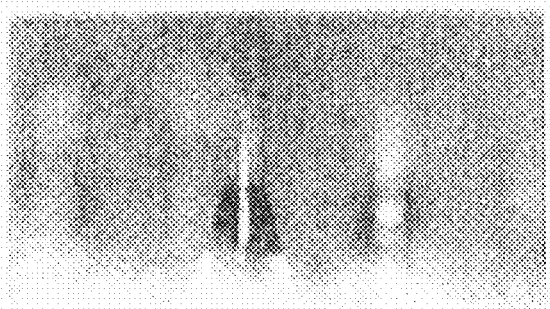
FIG. 14 is a photograph of the microneedle array produced in Example 16.

By the same procedures as in Example 13, coating of the solution C16 into each pore, centrifuging and drying, coating of the solution A16 into each pore, centrifuging (3,500 rpm, 15 minutes), centrifuging (3,500 rpm, 5 minutes), coating of the solution B16, pasting of the paper sheet, and centrifuging (3,500 rpm, 20 to 30 minutes) were carried out. The paper sheet was slowly peeled off and the needle-shaped solid stuff held on the paper sheet was removed from the mold. Consequently, a patch/microneedle array holding 100 microneedles was obtained. Any of the 100 microneedles held on the sheet had three sections as illustrated in FIGS. 5 and 6, namely, an acral portion composed from the base, a middle portion containing rifampicin, and a rear end portion. FIG. 14 shows a photograph of the obtained microneedle array.

In the same manner as in Example 1, one patch of the present example was pressed against the skin of 2 rats to administer rifampicin. Blood was collected from the jugular vein for 12 hours after administration, and systemic blood was collected. Plasma sample was prepared from each of the obtained blood sample. Rifampicin was extracted from the plasma sample by solid phase extraction method, and the concentration was measured using LC/MS/MS. The results are shown in Table 4. The values in the table are the mean value of 2 experiments. The results show that rifampicin was detected in the plasma.

TABLE 4

| | Time (hr) | | | | | | | |
|---|---|---|---|---|---|---|---|---|
| | 0 | 1 | 2 | 3 | 4 | 5 | 6 | 8 | 12 |
| Rifampicin concentration (ng/mL) | ND | 9.1 | 10.2 | 4.8 | 2.8 | 2.7 | 1.5 | 1.4 | 1.1 |

ND: Not detected

EXAMPLE 17

A viscous, dense solution (solution A17) was prepared by adding 40 µL of degassed purified water to 2.5 mg of leuprorelin acetate (Techno Science Japan Co., Ltd.; target substance), and 10.0 mg of chondroitin sulfate C sodium salt, and dissolving and mixing the resultant mixture. Further, a viscous solution (solution B17) was prepared by adding 750 µL of degassed purified water to 1.0 g of chondroitin sulfate C sodium salt, and dissolving and mixing the resultant mixture.

By the same procedures as in Example 14, coating of the solution A17 into each pore, centrifuging (3,500 rpm, 10 minutes), centrifuging (3,500 rpm, 5 minutes), coating of the solution B17, pasting of the paper sheet, and centrifuging (3,500 rpm, 30 minutes) were carried out. The paper sheet was slowly peeled off and the needle-shaped solid stuff held on the paper sheet was removed from the mold. Consequently, a patch/microneedle array holding 100 microneedles was obtained. Any of the 100 microneedles held on the sheet had two sections as illustrated in FIGS. 1 and 2, namely, an acral portion containing leuprorelin acetate and a rear end portion.

In the same manner as in Example 1, one patch of the present example was pressed against the skin of 2 rats to administer leuprorelin acetate. Blood was collected from the jugular vein for 4 hours after administration, and the systemic blood was collected. Plasma samples were prepared from the obtained blood samples. Leuprorelin acetate was extracted from the plasma sample by solid phase extraction method and the concentration was measured using LC/MS/MS. The results are shown in Table 5. The values in the table are the mean values of 2 examples. Specifically, good transdermal absorption of leuprorelin was shown.

TABLE 5

| | Time (min) | | | | | | |
|---|---|---|---|---|---|---|---|
| | 0 | 15 | 30 | 60 | 120 | 180 | 240 |
| Leuprorelin concentration (ng/mL) | ND | 10.3 | 12.7 | 5.3 | 1.4 | 0.6 | 0.3 |

ND: Not detected

EXAMPLE 18

A viscous, dense solution (solution A18) was prepared by adding 80 µL of degassed purified water to 5.0 mg of recombinant human growth hormone (Wako Pure Chemical Industries, Ltd.; target substance), 0.5 mg of lissamine green B, and 35 mg of high molecular weight dextran (base), and thoroughly dissolving and mixing the resultant mixture. Further, a viscous solution (solution B18) was prepared by adding 1.0 mL of degassed purified water to 1.0 g of high molecular weight dextran, and thoroughly dissolving and mixing the resultant mixture.

By the same procedures as in Example 14, coating of the solution A18 into each pore, centrifuging (3,500 rpm, 10 minutes), centrifuging (3,500 rpm, 5 minutes), coating of the solution B18, pasting of the paper sheet, and centrifuging (3,500 rpm, 30 minutes) were carried out. The paper sheet was slowly peeled off and the needle-shaped solid stuff held on the paper sheet was removed from the mold. Consequently, a patch/microneedle array holding 100 microneedles was obtained. Any of the 100 microneedles held on the sheet had two sections as illustrated in FIGS. 1 and 2, namely, an acral portion containing human growth hormone and a rear end portion. The acral portions were colored green due to the presence of the lissamine green B. The length L of the acral portions was approximately 250 µm.

EXAMPLE 19

A viscous, dense solution (solution A19) was prepared by adding 200 µL of degassed purified water to 0.5 mg of human basic fibroblast growth factor (bFGF; trade name: Fiblast Spray; Kaken Pharmaceutical Co., Ltd.; target substance) and 100 mg of pullulan (trade name: Pullulan PI-20; Hayashibara Biochemical Labs., Inc; base), and thoroughly dissolving and mixing the resultant mixture. Further, a viscous solution (solution B19) was prepared by adding 3.0 mL of degassed purified water to 1.5 g of pullulan, and thoroughly dissolving and mixing the resultant mixture.

By the same procedures as in Example 14, coating of the solution A19 into each pore, centrifuging (3,500 rpm, 10 minutes), centrifuging (3,500 rpm, 5 minutes), coating of the solution B19, pasting of the paper sheet, and centrifuging (3,500 rpm, 30 minutes) were carried out. The paper sheet was slowly peeled off and the needle-shaped solid stuff held on the paper sheet was removed from the mold. Consequently, a patch/microneedle array holding 100 microneedles was obtained. Any of the 100 microneedles held on the sheet had two sections as illustrated in FIGS. 1 and 2, namely, a tip portion containing human bFGF and a rear end portion.

EXAMPLE 20

A solution A19 (bFGF+pullulan) was prepared in the same manner as in Example 19. Lymphatic fluid was collected by cannulation of the thoracic lymph duct of rats who had been ingested with bovine milk previously. A lipid dispersion (solution A20) was prepared by adding 100 μL of this lymphatic fluid to the solution A20, and thoroughly mixing the resultant mixture. Further, a viscous solution (solution B20) was prepared by adding 3.0 mL of degassed purified water to 1.5 g of pullulan, and thoroughly dissolving and mixing the resultant mixture.

By the same procedures as in Example 14, coating of the solution A20 into each pore, centrifuging (3,500 rpm, 10 minutes), centrifuging (2,000 rpm, 5 minutes), coating of the solution B20, pasting of the paper sheet, and centrifuging (3,500 rpm, 30 minutes) were carried out. The paper sheet was slowly peeled off and the needle-shaped solid stuff held on the paper sheet was removed from the mold. Consequently, a patch/microneedle array holding 100 microneedles was obtained. Any of the 100 microneedles held on the sheet had two sections as illustrated in FIGS. 1 and 2, namely, a tip portion containing human bFGF (forming a complex with the lipids) and a rear end portion.

EXAMPLE 21

A viscous, dense solution was prepared by adding 200 μL of degassed purified water to 200 mg of high molecular weight dextran (Nacalai Tesque, Inc.; base). On the other hand, blood was separated by centrifugation, and the supernate, plasma, was collected. Then, the red blood cell (target substance) fraction was carefully collected. 100 μL of the red blood cell fraction was added to a dense solution of high molecular weight dextran, and was mixed (solution A21). Furthermore, a viscous solution (solution B21) was prepared by adding 1.0 mL of degassed purified water to 1.0 g of high molecular weight dextran, and thoroughly dissolving and mixing the resultant mixture.

By the same procedures as in Example 13, coating of the solution A21 into each pore, centrifuging (3,500 rpm, 10 minutes), centrifuging (3,500 rpm, 20 minutes), coating of the solution B21, pasting of the paper sheet, and centrifuging (3,500 rpm, 20 to 30 minutes) were carried out. The paper sheet was slowly peeled off and the needle-shaped solid stuff held on the paper sheet was removed from the mold. Consequently, a patch/microneedle array holding 100 microneedles was obtained. Any of the 100 microneedles held on the sheet had two sections as illustrated in FIGS. 1 and 2, namely, a tip portion containing red blood cells and a rear end portion.

EXAMPLE 22

A viscous, dense solution was prepared by adding 50 μL of distilled water to 0.5 mg of evans blue and 25 mg of chondroitin sulfate C sodium salt (base), and thoroughly dissolving and mixing the resultant mixture. Suspension (solution A22) was prepared by adding 5.0 mg of leuprorelin microcapsules (trade name: Leuplin for Injection 1.88; Takeda Pharmaceutical Company Limited; target substance) to the above thick liquid, and thoroughly mixing the resultant mixture. Further, dense solution (solution B22) was prepared by adding 750 μL of degassed purified water to 1.0 g of chondroitin sulfate C sodium salt, and thoroughly dissolving and mixing the resultant mixture. In addition, another viscous solution (solution C22) was prepared by adding 1.0 mL of degassed purified water to 1.0 g of chondroitin sulfate C sodium salt, and thoroughly dissolving and mixing the resultant mixture.

By the same procedures as in Example 13, coating of the solution C22 into each pore, centrifuging and drying, coating of the solution A22 into each pore, centrifuging (3,500 rpm, 5 minutes), centrifuging (3,500 rpm, 5 minutes), coating of the solution B22, pasting of the paper sheet, and centrifuging (3,500 rpm, 30 minutes) were carried out. The paper sheet was slowly peeled off and the needle-shaped solid stuff held on the paper sheet was removed from the mold. Consequently, a patch/microneedle array holding 100 microneedles was obtained. Any of the 100 microneedles held on the sheet had three sections as illustrated in FIGS. 5 and 6, namely, an acral portion made from the base, a middle portion containing leuprorelin microcapsules, and a rear end portion. The middle portions were colored blue due to the presence of evans blue.

EXAMPLE 23

A viscous, dense solution was prepared by adding 50 μL of distilled water to 0.5 mg of evans blue and 25 mg of high molecular weight dextran (base), and thoroughly dissolving and mixing the resultant mixture. Suspension (solution A23) was prepared by adding 5.0 mg of leuprorelin microcapsules (trade name: Leuplin for Injection 1.88; Takeda Pharmaceutical Company Limited; target substance) to the above thick liquid, and thoroughly mixing the resultant mixture. Furthermore, an adhesive solution (solution B23) was prepared by adding 750 μL of degassed purified water to 750 mg of high molecular weight dextran, and thoroughly dissolving and mixing the resultant mixture. In addition, a viscous solution (solution C23) was prepared by adding 1.0 mL of degassed purified water to 750 mg of high molecular weight dextran, and thoroughly dissolving and mixing the resultant mixture.

By the same procedures as in Example 13, coating of the solution C23 into each pore, centrifuging and drying, coating of the solution A23 into each pore, centrifuging (3,500 rpm, 5 minutes), centrifuging (3,500 rpm, 5 minutes), coating of the solution B23, pasting of the paper sheet, and centrifuging (3,500 rpm, 30 minutes) were carried out. The paper sheet was slowly peeled off and the needle-shaped solid stuff held on the paper sheet was removed from the mold. Consequently, a patch/microneedle array holding 100 microneedles was obtained. Any of the 100 microneedles held on the sheet had three sections as illustrated in FIGS. 5 and 6, namely, an acral portion formed from the base, a middle portion containing leuprorelin microcapsules, and a rear end portion. The middle portions were colored blue due to the presence of the evans blue.

EXAMPLE 24

A solution was prepared by adding 1.0 mL of purified water to 1.0 g of liposomal amphotericin B preparation (trade name: AmBisome; Dainippon Sumitomo Pharma Co., Ltd.) as a representative of a lipid dispersion preparation, and dissolving the resultant mixture by thoroughly shaking. Then, a viscous, dense solution (solution A24) was prepared by adding 0.7 g of chondroitin sulfate C sodium salt, and thoroughly mixing the resultant mixture. Further, a base solution (solution B24) was prepared by adding 1.0 mL of degassed purified water to 1.0 g of chondroitin sulfate C sodium salt, and thoroughly dissolving and mixing the resultant mixture.

A patch/microneedle array holding 100 microneedles was obtained in the same manner as in Example 5, except that the solution A24 was used instead of the solution A5, and the solution B24 was used instead of the solution B5. Any of the 100 microneedles held on the sheet had two sections as illustrated in FIGS. 1 and 2, namely, an acral portion containing liposomal amphotericin B and a rear end portion.

EXAMPLE 25

A viscous, dense solution (solution A25) was prepared by adding 40 μL of a 0.1 N sodium hydroxide solution and 30 μL of 0.15% evans blue to 7.5 mg of insulin sodium salt (self-prepared product; target substance), 2.5 mg of heparin sodium salt (Nacalai Tesque, Inc.), and 15 mg of dextran sulfate sodium salt (Wako Pure Chemical Industries, Ltd.; base), and thoroughly dissolving and mixing the resultant mixture. Further, a dense solution (solution B25) was prepared by adding 30 μL of purified water to 30 mg of dextran sulfate sodium salt, and thoroughly dissolving and mixing the resultant mixture.

Figure 15:
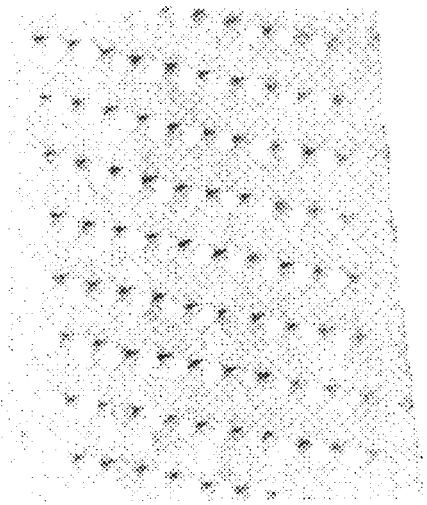
FIG. 15 is a photograph of the microneedle array produced in Example 25.

A patch/microneedle array holding 100 microneedles was obtained in the same manner as in Example 5, except that the solution A25 was used instead of the solution A5, and the solution B25 was used instead of the solution B5. Any of the 100 microneedles held on the sheet had two sections as illustrated in FIGS. 1 and 2, namely, an acral portion containing insulin sodium salt and a rear end portion. FIG. 15 shows a photograph of the obtained microneedle array.

Evaluation of the microneedles in the present example was carried out simultaneously with the following Example 26.

EXAMPLE 26

A viscous, dense solution (solution A26) was prepared by adding 30 μL of purified water to 10.0 mg of insulin sodium salt (self-prepared product; target substance) and 20 mg of chondroitin sulfate C sodium (Wako Pure Chemical Industries, Ltd.; base), and thoroughly dissolving and mixing the resultant mixture. Furthermore, a dense solution (solution B26) was prepared by adding 30 μL of purified water to 30 mg of chondroitin sulfate C sodium, and thoroughly dissolving and mixing the resultant mixture.

A patch/microneedle array holding 100 microneedles was obtained in the same manner as in Example 5, except that the solution A26 was used instead of the solution A5, and the solution B26 was used instead of the solution B5. Any of the 100 microneedles held on the sheet had two sections as illustrated in FIGS. 1 and 2, namely, an acral portion containing insulin sodium salt and a rear end portion.

An evaluation based on the rate of hypoglycemic effect in rats was carried out in the same manner as in Example 6 using the patches obtained in Examples 25 and 26. The results showed that the minimum blood glucose level after administration of the patch of Example 26 to the shaved abdominal skin of rats were obtained at about 4 hour after administration. On the other hand, for the patch of Example 25, the minimum blood glucose level was obtained at 1 hour after administration. This is considered that since the association of the insulin molecules occurs when the insulin content in the patch was increased, the dissolution/release rate after administration to the skin was decreased. However, by adding heparin and dextran sulfate sodium salt, the association of insulin molecules was decreased, so that the dissolution/release rate of insulin from the microneedle patch could be increased.

EXAMPLE 27

A solution A2 and a solution B2 were prepared in the same manner as in Example 2. Further, a dense solution (solution C2) was prepared by adding 1.0 mL of purified water to 300 mg of chondroitin sulfate C sodium salt, and thoroughly dissolving the resultant mixture.

The solution C2 was put on the tip of a 27G syringe needle, coated on each of the mold pores, and dried while centrifuging (3,000 rpm, 15 minutes). Consequently, the solution C2 was filled into the pores more towards the deeper end (tip side) of the pores, so that a space was formed at the near side (rear end side) of the pores. Then, in the same manner as in Example 1, the solution A2 was coated and filled into each of the mold pores, and then centrifuged (3,000 rpm, 5 minutes). Consequently, the solution A2 was filled into the pores, and superimposed over the solution C2. However, a space was left on the near side (rear end side) of the pores. The wrapping film was taken off, and residue on the mold surface was removed. Next, the solution B2 was thinly coated over the whole of the mold surface. In addition, the solution B2 was placed over each of the mold pores, and a paper sheet (support) was covered and pasted thereon. The mold was centrifuged by a table-top centrifuge (3,000 rpm, 30 minutes). Consequently, the solution B2 was filled into the pores, and superimposed over the solution A2. Simultaneously, the respective solutions in the mold were dried and solidified. The paper sheet was slowly peeled off and the needle-shaped solid stuff held on the paper sheet was removed from the mold. Consequently, a patch/microneedle array holding 100 microneedles was obtained. Any of the 100 microneedles held on the sheet had three sections as illustrated in FIGS. 5 and 6, namely, an acral portion formed from the base, a middle portion containing diclofenac sodium, and a rear end portion formed from only the base. The middle portions were colored white due to the presence of the diclofenac sodium. The total length L1 of the acral portion and the middle portion was approximately 350 μm.

EXAMPLE 28

In the present example, a comparative experiment was carried out between microneedles holding insulin in an acral portion only and conventional microneedles holding insulin in the whole preparation.

A patch/microneedle array holding 100 microneedles whose acral portions had a length of approximately 300 μm was obtained in the same manner as in Example 1. As a reference sample, using the same mold, a conventional patch/microneedle array was produced which held insulin in the whole preparation. The dimensions of each microneedle were accurately measured. Furthermore, the insulin content per patch was measured. The results are shown in Table 6. Refer to FIG. 2 regarding the total length H of the preparation, the diameter D of the pressing end, and the length L of the acral portion. Each value is the mean value of 100 microneedles. Specifically, the example and the reference sample had basically the same outer dimensions. Further, the example (1.7±0.2 μg/patch) had an insulin content of about 29% that of the reference sample (5.9±0.4 μg/patch).

TABLE 6

|  | H (μm) | D (μm) | L (μm) | Insulin content (μg/patch) |
|---|---|---|---|---|
| Example | 492.6 ± 2.4 | 290.0 ± 3.6 | 316.0 ± 7.3 | 1.7 ± 0.2 |
| Comparative example | 483.4 ± 4.7 | 292.2 ± 2.9 | — | 5.9 ± 0.4 |

An experiment was carried out by the same procedures as in Example 6 using rats, and the hypoglycemic effects for 5 hours after administration were measured. The results showed that, for the microneedles of the example, the total blood glucose decrease area (1 to 5 hours) was 149.7±8.0% hr, and for the microneedles of the reference sample, the value was 159.8±30.6% hr. By a statistical analysis using a significance test, no significant difference was found out between the two preparations. Based on the above results, it was shown that the microneedles of the example having lower insulin content (approximately 29% of that contained in the reference sample) showed the same pharmacological effect as the microneedles of the reference sample Furthermore, the pharmacological availability was calculated to be 30.7±1.9% for the microneedles of the example and 9.2±1.6% for the microneedles of the reference sample. Accordingly, the microneedles of the example were superior in this point too.

EXAMPLE 29

In the present example, a comparative study was carried out between microneedles holding erythropoietin in the acral portion only and conventional microneedles holding erythropoietin in the whole preparation.

Erythropoietin injection solution was concentrated by a factor of two under the flow of nitrogen gas. A viscous, dense solution (solution A29) was prepared by kneading 46 μl, of thus obtained dense solution, 0.5 mg of evans blue, 22.5 mg of chondroitin sulfate C sodium salt (base), and 22.5 mg of high molecular weight dextran. A patch/microneedle array holding 100 microneedles was obtained in the same manner as in Example 7, except that the solution A29 was used instead of the solution A7. Any of the 100 microneedles held on the sheet had two sections as illustrated in FIGS. 1 and 2, namely, an acral portion containing EPO and a rear end portion containing the adhesive substance. As a reference experiment, using the same mold, a conventional patch/microneedle array holding 100 microneedles which held erythropoietin in the whole preparation was produced.

Figure 16:
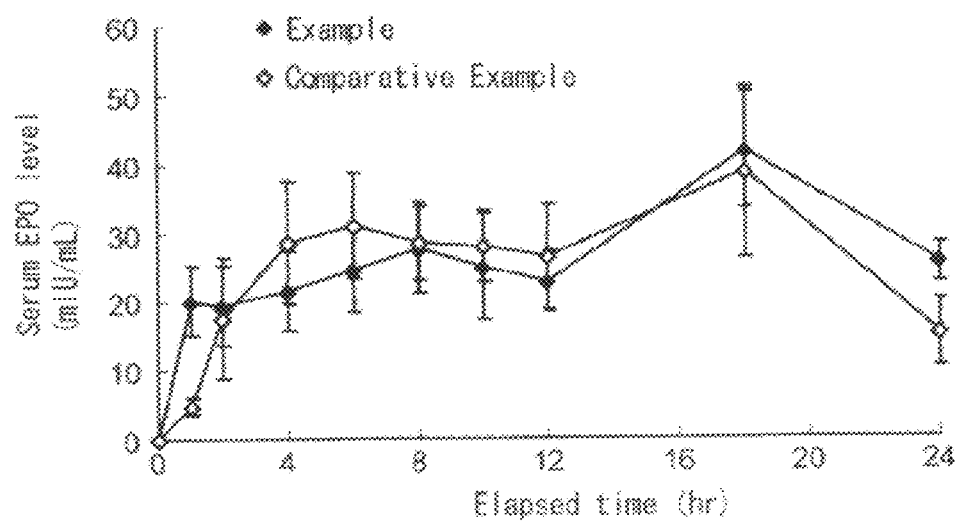
FIG. 16 is a graph showing the temporal transitions of serum EPO level after the microneedles produced in Example 29 were administered to a rat.

An experiment was carried out using 3 rats per group by the same procedures as in Example 8. Blood was collected from the jugular vein for 24 hours after administration to measure the changes in EPO levels in the serum. The results are shown in FIG. 16. In FIG. 16, the black diamond shape indicates the data for the microneedle array (patch) of the example, and the white diamond shape indicates the data for the microneedle array (patch) of the reference experiment. The value of the area under the blood EPO level-time curve AUC was 667.1±125.1 (SE) mIU hr/mL for the example, and 648.0±91.7 (SE) mIU hr/mL for the reference experiment. No significant difference was detected. The results of the content experiment showed that the example preparation containing EPO in the tip portions contained 20.6±5.1 IU. The EPO content for the reference experiment preparation was 102±20.9 IU. From the above result, it was shown that the microneedles of the example containing EPO in the acral portions with a lower erythropoietin content exhibited the same pharmacokinetics as that of the microneedles of the reference experiment which contained EPO throughout.

EXAMPLE 30

Based on the method of Example 1, a total of 4 kinds of microneedles were prepared whose total lengths H were 200, 300, 400, and 500 μm, respectively. These microneedles were inserted into the skin of the arm by pressing with a finger. The results were that there was no blood leakage or pain for any of the microneedles.

The invention claimed is:

1. A needle-shaped preparation for body surface application, comprising:
   a base formed from a biosoluble substance and containing a target substance, the preparation being configured to be inserted into a body surface, and the target substance being capable of being absorbed into the body by dissolution of the base,
   wherein the preparation comprises at least a first section and a second section divided by an interface in an insertion direction;
   the second section is the rearmost end section of the preparation in the insertion direction;
   the first section contains the target substance evenly distributed therein;
   the first section is a solidified first liquid base in which the target substance is dissolved;
   the second section is a solidified second liquid base not containing the target substance; and
   the solidified first liquid base and the solidified second liquid base have different compositions which were prepared separately.

2. A needle-shaped preparation for body surface application, comprising:
   a base formed from a biosoluble substance and containing a target substance, the preparation being configured to be inserted into a body surface, and the target substance being capable of being absorbed into the body by dissolution of the base,
   wherein the preparation comprises at least a first section and a second section divided by an interface in an insertion direction;
the second section is the rearmost end section of the preparation in the insertion direction;
the first section contains the target substance evenly distributed therein;
the first section is:
   (a) a solidified first liquid base in which cells are dispersed,
   (b) a solidified first liquid base in which the target substance is dispersed as a lipid dispersion, or
   (c) a solidified first liquid base in which the target substance formed from fine particles having an average particle size of 10 micrometers or less is dispersed therein;
the second section is a solidified second liquid base not containing the target substance; and
the solidified first liquid base and the solidified second liquid base have different compositions which were prepared separately.

3. The preparation for body surface application according to claim 1 or 2, wherein the first section is the frontmost end section.

4. The preparation for body surface application according to claim 1 or 2, wherein the total length in the insertion direction is in a range of 200 to 600 micrometers.

5. The preparation for body surface application according to claim 4, wherein the total length in the insertion direction is in a range of 400 to 600 micrometers.

6. The preparation for body surface application according to claim 5, wherein a sum of the lengths in the insertion direction of the sections excluding the rearmost end section is 350 micrometers or less.

7. A needle-shaped preparation for body surface application, comprising:
a base formed from a biosoluble substance and containing a target substance, the preparation being configured to be inserted into a body surface, and the target substance being capable of being absorbed into the body by dissolution of the base,
wherein the preparation comprises at least a first section, a second section and a third section divided by interfaces in an insertion direction;
the first section contains the target substance and is not either the frontmost end section or the rearmost end section of the preparation in the insertion direction; and
the first section is a solidified first liquid base in which the target substance is dissolved or evenly dispersed therein;
the second section is a solidified second liquid base not containing the target substance; and
the solidified first liquid base and the solidified second liquid base have different compositions which were prepared separately.

8. The preparation for body surface application according to claim 7, wherein the first section is adjacent to the frontmost end section.

9. The preparation for body surface application according to claim 7 or 8, wherein the total length in the insertion direction is in a range of 200 to 600 micrometers.

10. The preparation for body surface application according to claim 9, wherein the total length in the insertion direction is in a range of 400 to 600 micrometers.

11. The preparation for body surface application according to claim 10, wherein a sum of the lengths in the insertion direction of the sections excluding the rearmost end section is 350 micrometers or less.

12. The preparation for body surface application according to claim 7 or 8, wherein the target substance is
encapsulated in a microcapsule or comprises
fine particles having an average particle size of 10 micrometers or less.

13. The preparation for body surface application according to any one of claim 1, 2, or 7, wherein the body surface comprises skin, cornea, oral soft tissue, gum, or nasal cavity mucous membrane.

14. The preparation for body surface application according to any one of claim 1, 2, or 7, wherein the base is a high molecular weight substance.

15. The preparation for body surface application according to claim 14, wherein the high molecular weight substance is at least one selected from the group consisting of polysaccharide, protein, polyvinyl alcohol, carboxy vinyl polymer, a copolymer thereof, and a salt thereof.

16. The preparation for body surface application according to any one of claim 1, 2, or 7, wherein the target substance comprises a peptide, a protein, a nucleic acida, or a polvsaccharide.

17. The preparation for body surface application according to any one of claim 1, 2, or 7, wherein the target substance comprises a drug, a vaccine, a nutrient, or a cosmetic component.

18. The preparation for body surface application according to any one of claim 1, 2, or 7, wherein the base includes a porous substance, and the target substance is held in the porous substance, so that the target substance can be sustained-released.

19. A preparation for body surface application-holding sheet, in which one or two or more of the preparation for body surface application according to any one of claim 1, 2, or 7 are held on at least one surface of a sheet-like support, wherein the preparation for body surface application is configured to be inserted into a body surface by pressing against the body surface.

20. The preparation for body surface application-holding sheet according to claim 19, wherein the preparation for body surface application includes an adhesive substance in the rearmost end section.

* * * * *